(12) United States Patent
Miyoshi et al.

(10) Patent No.: US 10,575,087 B2
(45) Date of Patent: Feb. 25, 2020

(54) PICKUP SENSOR AND BIOLOGICAL SENSOR

(71) Applicant: FUJIFILM Corporation, Tokyo (JP)

(72) Inventors: Tetsu Miyoshi, Ashigara-kami-gun (JP); Jun Sato, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/231,755

(22) Filed: Dec. 24, 2018

(65) Prior Publication Data

US 2019/0141433 A1     May 9, 2019

Related U.S. Application Data

(63) Continuation of application No. PCT/JP2017/021962, filed on Jun. 14, 2017.

(30) Foreign Application Priority Data

Jul. 27, 2016    (JP) ................. 2016-147653

(51) Int. Cl.
    *H04R 1/14*        (2006.01)
    *H01L 41/193*     (2006.01)
    (Continued)

(52) U.S. Cl.
    CPC ............... *H04R 1/14* (2013.01); *G10H 3/143* (2013.01); *H01L 41/053* (2013.01);
    (Continued)

(58) Field of Classification Search
    CPC .......... H04R 1/14; H04R 17/025; H04R 1/46; G10H 3/143; G10H 2220/545; H01L 41/0805; H01L 41/1132; H01L 41/193
    (Continued)

(56) References Cited

U.S. PATENT DOCUMENTS

| | | | | |
|---|---|---|---|---|
| 4,843,275 A | * | 6/1989 | Radice | ................. H04R 17/025 310/334 |
| 5,757,090 A | * | 5/1998 | Kirjavainen | ........... H04R 19/00 29/592.1 |

(Continued)

FOREIGN PATENT DOCUMENTS

| | | |
|---|---|---|
| JP | 52-57493 U | 4/1977 |
| JP | 55-74198 U | 5/1980 |

(Continued)

OTHER PUBLICATIONS

International Search Report (PCT/ISA/210) issued in PCT/JP2017/021962, dated Sep. 5, 2017.
(Continued)

*Primary Examiner* — Sean H Nguyen
(74) *Attorney, Agent, or Firm* — Birch, Stewart, Kolasch & Birch, LLP

(57) ABSTRACT

Provided are a pickup sensor and a biological sensor that are small-sized and can detect micro vibration efficiently and stably with high accuracy. The pickup sensor includes an electroacoustic converter film including: a piezoelectric polymer composite in which piezoelectric particles are dispersed in a viscoelastic matrix that is formed of a polymer material having viscoelasticity at normal temperature; two thin film electrodes that are laminated on opposite surfaces of the piezoelectric polymer composite, respectively; and a protective layer that is laminated on at least one of the two thin film electrodes, in which at least a part of a surface of the electroacoustic converter film is an abutting surface that abuts against a test object, and the thin film electrode on a surface opposite to the abutting surface is grounded.

16 Claims, 10 Drawing Sheets

(51) Int. Cl.
  *H04R 17/02* (2006.01)
  *H01L 41/08* (2006.01)
  *G10H 3/14* (2006.01)
  *H01L 41/113* (2006.01)
  *H04R 7/10* (2006.01)
  *H01L 41/18* (2006.01)
  *H01L 41/053* (2006.01)
  *H04R 1/46* (2006.01)
  *H04R 1/28* (2006.01)

(52) U.S. Cl.
  CPC ...... *H01L 41/0805* (2013.01); *H01L 41/1132* (2013.01); *H01L 41/183* (2013.01); *H01L 41/193* (2013.01); *H04R 7/10* (2013.01); *H04R 17/025* (2013.01); *G10H 2220/371* (2013.01); *G10H 2220/535* (2013.01); *G10H 2220/545* (2013.01); *H04R 1/2869* (2013.01); *H04R 1/46* (2013.01)

(58) Field of Classification Search
  USPC .......................................................... 381/190
  See application file for complete search history.

(56) References Cited

U.S. PATENT DOCUMENTS

| | | | |
|---|---|---|---|
| 6,486,588 B2 * | 11/2002 | Doron | A61B 5/0031 310/321 |
| 2003/0028110 A1 * | 2/2003 | Toda | A61B 7/04 600/437 |
| 2014/0210309 A1 * | 7/2014 | Miyoshi | H04R 7/04 310/313 A |
| 2015/0156583 A1 * | 6/2015 | Mulumudi | H04R 1/46 381/67 |

FOREIGN PATENT DOCUMENTS

| | | |
|---|---|---|
| JP | 2013-153364 A | 8/2013 |
| JP | 2014-14063 A | 1/2014 |
| JP | 2014-195132 A | 10/2014 |

OTHER PUBLICATIONS

Written Opinion of the International Searching Authority (PCT/ISA/273) issued in PCT/JP2017/021962, dated Sep. 5, 2017.

* cited by examiner

PICKUP SENSOR AND BIOLOGICAL SENSOR

CROSS-REFERENCE TO RELATED APPLICATIONS

This application is a Continuation of PCT International Application No. PCT/JP2017/021962 filed on Jun. 14, 2017, which claims priority under 35 U.S.C. § 119(a) to Japanese Patent Application No. 2016-147653 filed on Jul. 27, 2016. The above application is hereby expressly incorporated by reference, in its entirety, into the present application.

BACKGROUND OF THE INVENTION

1. Field of the Invention

The present invention relates to a pickup sensor and a biological sensor.

2. Description of the Related Art

A throat microphone in which a piezoelectric element is used as a vibration detection portion is known.

The throat microphone is used in a state where the vibration detection portion is pressed against a throat, and detects vibration of the throat.

For example, JP2013-153364A discloses a throat microphone including: a first vibration-to-electricity converter that is pressed against a throat through a holding member for a human body and converts vibration generated from the throat into a sound signal; and a second vibration-to-electricity converter that detects mechanical vibration applied to the holding member as an electrical noise signal, in which a sound output level of the first vibration-to-electricity converter is controlled by the second vibration-to-electricity converter.

In addition, JP2014-195132A discloses a throat microphone including: a first piezoelectric bimorph; a second piezoelectric bimorph that has a resonance frequency different from that of the first piezoelectric bimorph; a first impedance converter that converts an output impedance of a signal output from the first piezoelectric bimorph; a second impedance converter that converts an output impedance of a signal output from the second piezoelectric bimorph; and a first buffer circuit and a second buffer circuit to which the signal output from the first impedance converter and the signal output from the second impedance converter are input, respectively, in which the first piezoelectric bimorph and the second piezoelectric bimorph are attached to a common base, the output signal of the first buffer circuit and the output signal of the second buffer circuit are independent from each other, and the output signal of the first buffer circuit and the output signal of the second buffer circuit are output in a balanced state.

On the other hand, JP2014-014063A describes that an electroacoustic converter film is used as a vocal cord microphone, the electroacoustic converter film including: a piezoelectric polymer composite in which piezoelectric particles are dispersed in a viscoelastic matrix that is formed of a polymer material having viscoelasticity at normal temperature; and thin film electrodes that are formed on opposite surfaces of the piezoelectric polymer composite, respectively.

Here, since the throat microphone is worn on a throat, reduction in size is required.

However, in a throat microphone in which a piezoelectric element is used as a vibration detection portion as described in JP2013-153364A and JP2014-195132A, in order to prevent unpleasant noise generated during contact with the throat microphone, for example, during wearing of the throat microphone, a second sensor for detecting a noise signal and a signal processing circuit or the like are required. Therefore, there is a problem in that it is difficult to reduce the size of the device.

On the other hand, the electroacoustic converter film described in JP2014-014063A has no in-plane anisotropy in piezoelectric characteristics, and thus can detect vibration of a throat by being directly bonded to the throat. In addition, since the electroacoustic converter film is not likely to resonate, unpleasant noise is not likely to occur during contact. Therefore, the second sensor and the signal processing circuit or the like are not necessary. Thus, it is easy to reduce the size of the device, and the electroacoustic converter film can be suitably used as a throat microphone.

SUMMARY OF THE INVENTION

However, according to an investigation by the present inventors, it was found that, in a case where the electroacoustic converter film disclosed in JP2014-014063A is used as a throat microphone, the throat microphone is weak to external electromagnetic noise, picks up, for example, noise of a commercial power source, and has a problem in that it is difficult to detect micro vibration efficiently and stably with high accuracy.

An object of the present invention is to solve the above-described problem of the related art and to provide a pickup sensor and biological sensor that are small-sized and can detect micro vibration efficiently and stably with high accuracy.

The present inventors conducted a thorough investigation in order to achieve the above-described object and found that the above-described object can be achieved with a pickup sensor film including an electroacoustic converter film including: a piezoelectric polymer composite in which piezoelectric particles are dispersed in a viscoelastic matrix that is formed of a polymer material having viscoelasticity at normal temperature; two thin film electrodes that are laminated on opposite surfaces of the piezoelectric polymer composite, respectively; and a protective layer that is laminated on at least one of the two thin film electrodes, in which at least a part of a surface of the electroacoustic converter film is an abutting surface that abuts against a test object, and the thin film electrode on a surface opposite to the abutting surface is grounded. Based on the above finding, the present invention has been completed.

That is, the present invention provides a pickup sensor and a biological sensor having the following configuration.

(1) A pickup sensor comprising an electroacoustic converter film including:

a piezoelectric polymer composite in which piezoelectric particles are dispersed in a viscoelastic matrix that is formed of a polymer material having viscoelasticity at normal temperature;

two thin film electrodes that are laminated on opposite surfaces of the piezoelectric polymer composite, respectively; and a protective layer that is laminated on at least one of the two thin film electrodes, wherein at least a part of a surface of the electroacoustic converter film is an abutting surface that abuts against a test object, and the thin film electrode on a surface opposite to the abutting surface is grounded.

(2) The pickup sensor according to (1),
in which one main surface of the electroacoustic converter film where the protective layer is laminated is the abutting surface, and
the thin film electrode that is laminated on another main surface is grounded.

(3) The pickup sensor according to (1),
in which the electroacoustic converter film is folded, and
the thin film electrode that is laminated on an outside main surface of the folded electroacoustic converter film is grounded.

(4) The pickup sensor according to (3),
in which the protective layer is laminated on an outside main surface of the folded electroacoustic converter film.

(5) The pickup sensor according to any one of (1) to (4),
in which the electroacoustic converter film is curved and held so as to protrude to one main surface.

(6) The pickup sensor according to any one of (1) to (5), further comprising:
an elastic support that is disposed to adhere to one main surface of the electroacoustic converter film such that the electroacoustic converter film is curved,
in which the elastic support is disposed to adhere to a main surface of the electroacoustic converter film on the grounded thin film electrode side.

(7) The pickup sensor according to any one of (1) to (6), further comprising:
an elastic holding member that is formed in a C-shape,
in which the holding member presses and holds the electroacoustic converter film against the test object.

(8) The pickup sensor according to any one of (1) to (7), further comprising:
a suction cup member,
in which the electroacoustic converter film is disposed at a center of an adsorption surface of the suction cup member.

(9) A biological sensor comprising:
the pickup sensor according to any one of (1) to (8).

According to the present invention, it is possible to provide a pickup sensor and a biological sensor that are small-sized and can detect micro vibration efficiently and stably with high accuracy.

DESCRIPTION OF THE PREFERRED EMBODIMENTS

Hereinafter, a pickup sensor and a biological sensor according to the present invention will be described in detail based on a preferable embodiment shown in the accompanying drawings.

The following description regarding components has been made based on a representative embodiment of the present invention. However, the present invention is not limited to the embodiment.

In this specification, numerical ranges represented by "to" include numerical values before and after "to" as lower limit values and upper limit values.

In addition, in this specification, main surfaces refer to, among all the surfaces of a film, opposite two surfaces having much larger areas than other surfaces.

The pickup sensor according to the embodiment of the present invention includes an electroacoustic converter film including:
a piezoelectric polymer composite in which piezoelectric particles are dispersed in a viscoelastic matrix that is formed of a polymer material having viscoelasticity at normal temperature;
two thin film electrodes that are laminated on opposite surfaces of the piezoelectric polymer composite, respectively; and
a protective layer that is laminated on at least one of the two thin film electrodes, in which at least a part of a surface of the electroacoustic converter film is an abutting surface that abuts against a test object, and the thin film electrode on a surface opposite to the abutting surface is grounded.

In addition, the biological sensor according to the embodiment of the present invention is formed of the pickup sensor.

The pickup sensor according to the embodiment of the present invention detects vibration in a test object. For example, the pickup sensor is attached to a throat of a human body and is used as a throat microphone that detects vibration generated from the throat and outputs the detected vibration as a sound signal.

Alternatively, the pickup sensor according to the embodiment of the present invention is attached to any position of a biological body and is used as a biological sensor such as a pulsimeter, a heart rate meter, a stethoscope, or a sphygmomanometer that measures a pulse rate or a heart rate.

Alternatively, the pickup sensor according to the embodiment of the present invention is attached to a test object site of each of various devices and measures vibration to detect abnormality such that it is used as a sensor for the device for evaluating whether or not malfunction occurs in the test object site. For example, the pickup sensor is attached to a bearing of a device to measure vibration, and in a case where the vibration is more than a threshold, the pickup sensor evaluates that the bearing is damaged by abrasion.

That is, in the present invention, a test object T is a human body or various devices.

Figure 1:
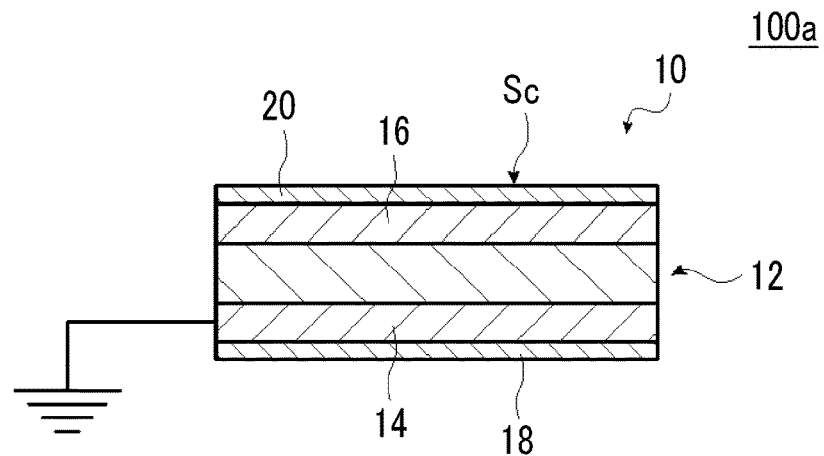
FIG. 1 is a cross-sectional view schematically showing an example of a pickup sensor according to the present invention.

FIG. 1 is a cross-sectional view schematically showing an example of the pickup sensor according to the embodiment of the present invention.

A pickup sensor 100a shown in FIG. 1 includes an electroacoustic converter film (hereinafter, also referred to as "converter film") 10, in which a (lower) thin film electrode 14 on a surface of the converter film 10 opposite to an abutting surface Sc abutting against the test object is grounded.

Figure 2:
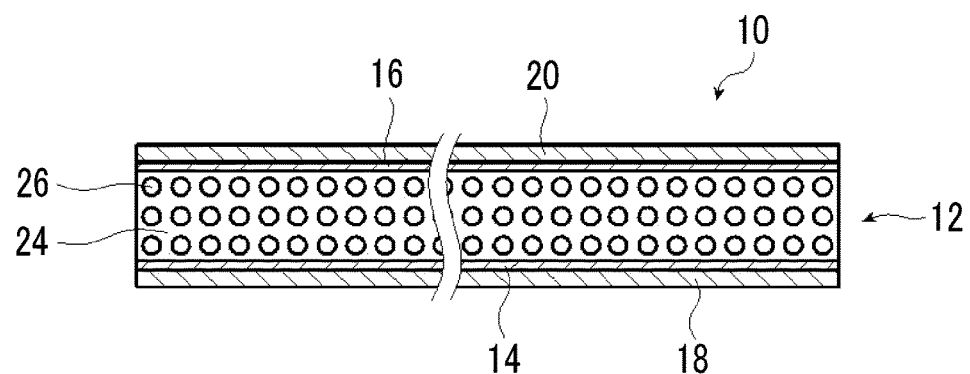
FIG. 2 is a cross-sectional view schematically showing an example of an electroacoustic converter film.

FIG. 2 is a cross-sectional view schematically showing an example of the converter film 10.

As shown in FIG. 2, the converter film 10 includes: a piezoelectric layer 12 that is a sheet-like material having piezoelectricity; the lower thin film electrode 14 that is laminated on one surface of the piezoelectric layer 12; a lower protective layer 18 that is laminated on the lower thin film electrode 14; an upper thin film electrode 16 that is laminated on another surface of the piezoelectric layer 12; and an upper protective layer 20 that is laminated on the upper thin film electrode 16.

In the converter film 10, the piezoelectric layer 12 is formed of a piezoelectric polymer composite.

As conceptually seen from FIG. 2, in the piezoelectric polymer composite which forms the piezoelectric layer 12, piezoelectric particles 26 are dispersed in a viscoelastic matrix 24 that is formed of a polymer material having viscoelasticity at normal temperature "Normal temperature" described in this specification refers to a temperature range of about 0° C. to 50° C.

In addition, the lower thin film electrode 14 and the upper thin film electrode 16 form a pair of electrodes and are laminated on main surfaces of the piezoelectric layer 12, respectively, such that the piezoelectric layer 12 is interposed therebetween.

The converter film 10 having the above-described configuration has piezoelectricity and converts an expansion and contraction movement of the film caused by the vibration of the test object into an electrical signal.

The details of the converter film 10 will be described below.

Here, in the pickup sensor 100a shown in FIG. 1, the main surface on which the upper protective layer 20 is laminated is set as the abutting surface Sc abutting against the test object, and the lower thin film electrode 14 as the thin film electrode that is laminated on the main surface opposite to the abutting surface Sc is grounded.

Figure 3:
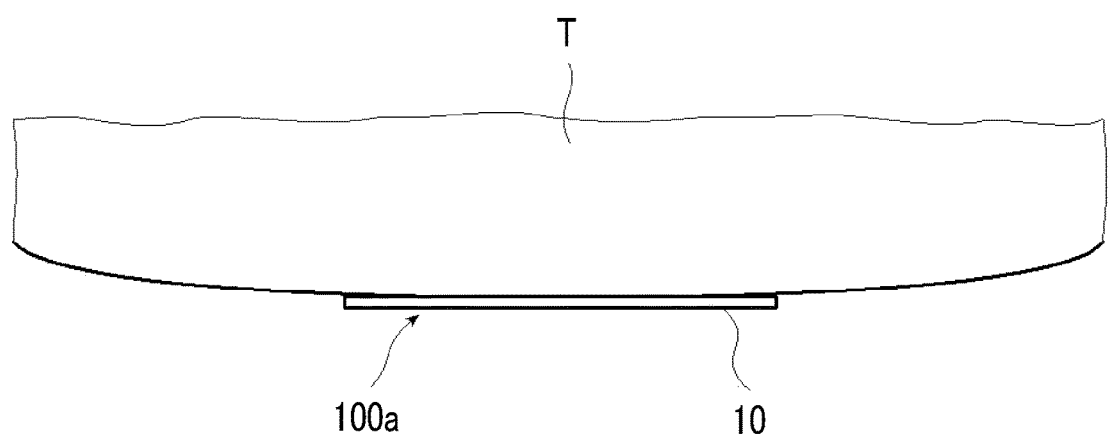
FIG. 3 is a cross-sectional view schematically showing an example where the pickup sensor shown in FIG. 1 is disposed in a test object.

As shown in FIG. 3, the pickup sensor 100a is provided such that the abutting surface Sc is in contact with the test object T. Accordingly, the grounded lower thin film electrode 14 is positioned on the farther side from the test object T. Therefore, the piezoelectric layer 12 is positioned between the test object T and the lower thin film electrode 14.

That is, in a case where the test object T side is set as the inside, an outside thin film electrode of the piezoelectric layer 12 is grounded.

As described above, in a throat microphone in which a piezoelectric element of the related art is used as a vibration detection portion, in order to prevent unpleasant noise generated during contact with the throat microphone, for example, during wearing of the throat microphone, a second sensor for detecting a noise signal and a signal processing circuit or the like are required. Therefore, there is a problem in that it is difficult to reduce the size of the device.

On the other hand, in an electroacoustic converter film can detect vibration of a throat by being directly bonded to the throat, the electroacoustic converter film including: a piezoelectric polymer composite in which piezoelectric particles are dispersed in a viscoelastic matrix that is formed of a polymer material having viscoelasticity at normal temperature; and thin film electrodes that are formed on opposite surfaces of the piezoelectric polymer composite, respectively. In addition, since the electroacoustic converter film is not likely to resonate, unpleasant noise is not likely to occur during contact. Therefore, the second sensor and the signal processing circuit or the like are not necessary. Therefore, it is easy to reduce the size of the device.

However, according to an investigation by the present inventors, it was found that, in a case where the electroacoustic converter film is used, the throat microphone is weak to external electromagnetic noise, picks up, for example, noise of a commercial power source, and has a problem in that it is difficult to detect micro vibration efficiently and stably with high accuracy.

On the other hand, the pickup sensor according to the embodiment of the present invention includes an electroacoustic converter film including: a piezoelectric polymer composite in which piezoelectric particles are dispersed in a viscoelastic matrix that is formed of a polymer material having viscoelasticity at normal temperature; and two thin film electrodes that are laminated on opposite surfaces of the piezoelectric polymer composite, respectively; and a protective layer that is laminated on at least one of the two thin film electrodes, in which at least a part of a surface of the electroacoustic converter film is an abutting surface that abuts against a test object, and the thin film electrode on a surface opposite to the abutting surface is grounded.

With the above-described configuration, the outside thin film electrode functions as an electromagnetic shield to electromagnetic noise generated from an external device such as a commercial power source. As a result, the piezoelectric layer positioned inside the outside thin film electrode can be prevented from being affected by an external electromagnetic noise. Since the noise can be reduced, even in a case where vibration to be detected is micro vibration, the micro vibration can be detected efficiently and stably with high accuracy.

From the viewpoint that weak vibration can be detected with high accuracy, the pickup sensor according to the embodiment of the present invention can be suitably used as a biological sensor such as a pulsimeter, a heart rate meter, a stethoscope, or a sphygmomanometer that measures a pulse rate or a heart rate of a biological body (human body or animal).

In addition, the converter film used in the embodiment of the present invention is small-sized, lightweight, has excellent flexibility, and has little variation in sound quality during deformation. Therefore, the converter film can be easily bonded to any position of a human body having a complex curved surface and to any position of various devices. In addition, the converter film is small-sized and lightweight, and thus can be bonded to a narrow position of various devices.

A method of bonding the pickup sensor according to the embodiment of the present invention to the test object is not particularly limited, and various well-known bonding method to a sheet-like material can be used.

In addition, instead of directly bonding the pickup sensor to the test object, the pickup sensor may be bonded to the test object in a state where the converter film is accommodated in an extremely thin case or bag.

Here, in the pickup sensor shown in FIG. 1, one main surface of the converter film 10 is set as the abutting surface Sc, and the thin film electrode on another main surface side of the converter film 10 is grounded. However, the embodiment is not limited to this configuration.

Figure 4:
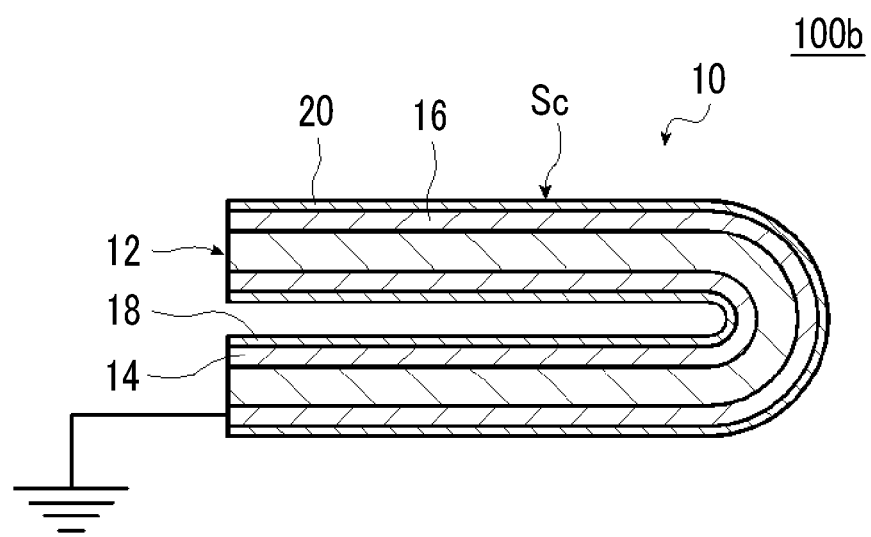
FIG. 4 is a cross-sectional view schematically showing another example of the pickup sensor according to the present invention.

FIG. 4 is a cross-sectional view schematically showing another example of the pickup sensor according to the embodiment of the present invention.

A pickup sensor 100b shown in FIG. 4 includes one converter film 10, in which the electroacoustic converter film 10 is folded, and the upper thin film electrode 16 as a thin film electrode that is laminated on an outside main surface of the folded electroacoustic converter film 10 is grounded. In addition, one of outside main surfaces of the folded converter film 10 is the abutting surface Sc. As shown in the drawing, in the pickup sensor 100b, a thin film electrode on a side close to the abutting surface Sc is also the grounded upper thin film electrode 16, and an inside thin film electrode of the folded converter film 10 is the lower thin film electrode 14.

In a case where the converter film 10 is folded and used as in the case of the pickup sensor 100b shown in FIG. 4, the thin film electrode close to the side among the opposite outsides of the folded converter film 10 is grounded. Therefore, the piezoelectric layer 12 can be prevented from being affected not only by an external electromagnetic noise but also an electromagnetic noise incident from the test object T side such as a human body.

For easy understanding of the description, FIG. 4 shows a state where the converter film 10 is not completely folded. However, the inside main surfaces of the folded converter film 10 may adhere to each other.

In the pickup sensor 100a shown in FIG. 1 and the pickup sensor 100b shown in FIG. 4, protective layers are provided on opposite surfaces of the converter film 10, respectively. However, the embodiment is not limited to this configuration, and the protective layer may be provided on at least the abutting surface Sc. It is preferable that the protective layers are provided on opposite surfaces, respectively. That is, in the pickup sensor 100a shown in FIG. 1, the abutting surface Sc is opposite to the grounded lower thin film electrode 14. Therefore, the protective layer (upper protective layer 20) may be provided on the upper thin film electrode 16 side. In addition, in the pickup sensor 100b shown in FIG. 4, the outside main surface as the abutting surface Sc is the surface on the grounded upper thin film electrode 16 side. Therefore, the protective layer (upper protective layer 20) may be provided on the upper thin film electrode 16 side.

A replaceable second protective layer may be inserted into the protective layer and the test object T on the abutting surface Sc.

In addition, as described above, instead of directly bonding the pickup sensor to the test object, the pickup sensor may be bonded to the test object in a state where the converter film is accommodated in an extremely thin case.

Figure 5:
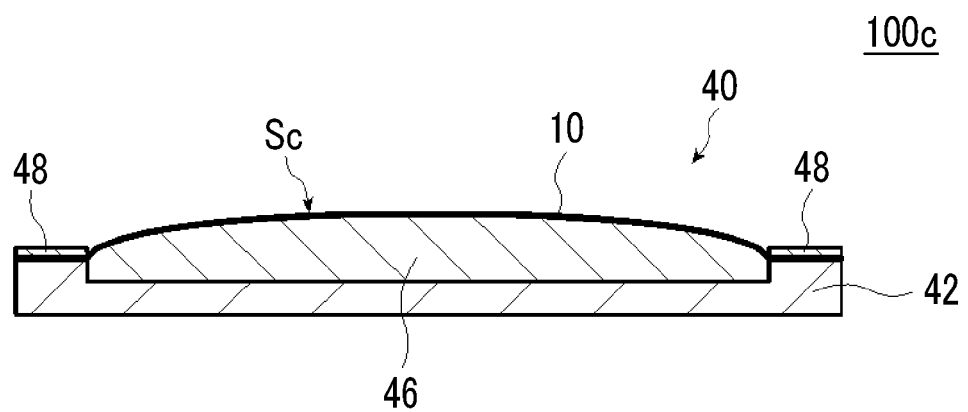
FIG. 5 is a cross-sectional view schematically showing still another example of the pickup sensor according to the present invention.
Figure 6:
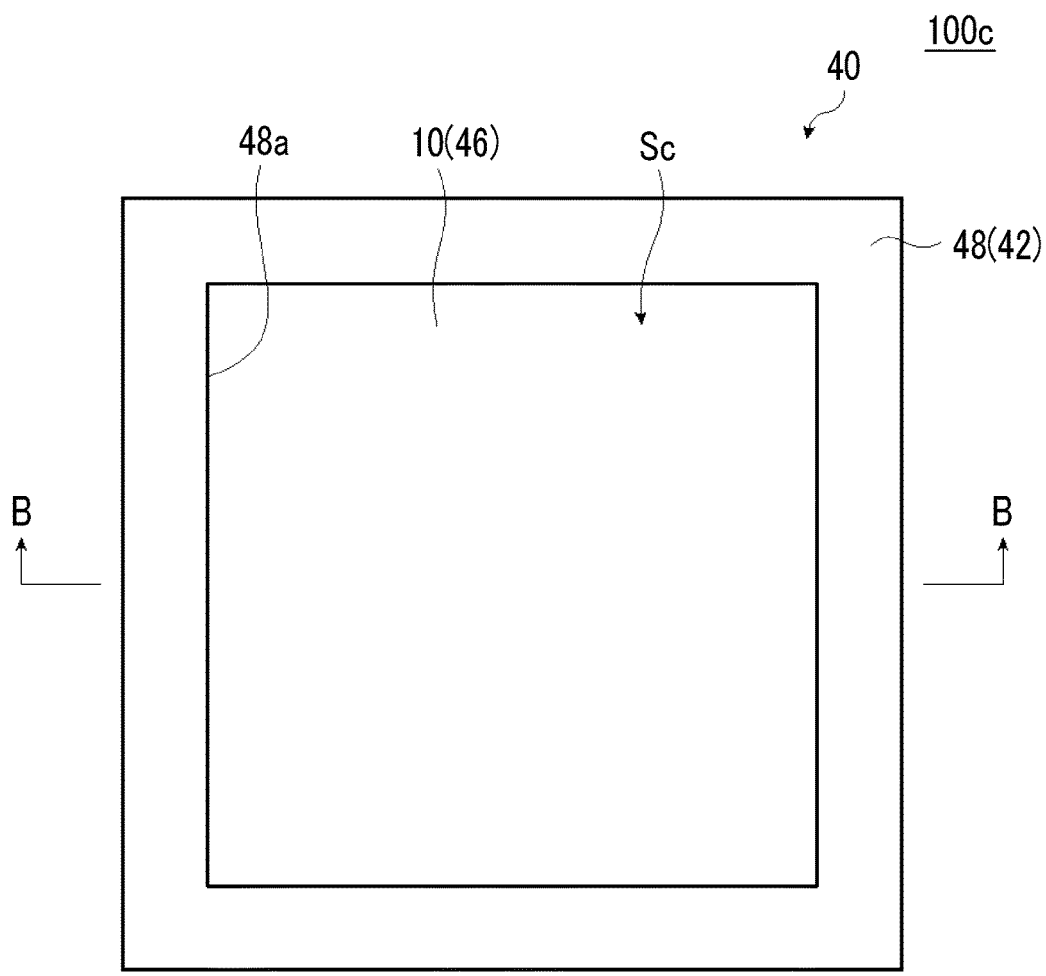
FIG. 6 is a top view showing the pickup sensor shown in FIG. 5.

FIG. 5 is a cross-sectional view schematically showing still another example of the pickup sensor according to the embodiment of the present invention. FIG. 6 is a top view showing the pickup sensor shown in FIG. 5. That is, FIG. 5 is a cross-sectional view taken along line B-B of the pickup sensor shown in FIG. 6.

A pickup sensor 100c shown in FIG. 5 includes an electroacoustic converter unit (hereinafter, also referred to as "converter unit") 40 including the converter film 10, a case 42, a viscoelastic support 46, and a pressing member 48, and the viscoelastic support 46 is disposed to adhere to the main surface of the converter film 10 on the grounded thin film electrode side. That is, a main surface of the converter film 10 opposite to the main surface adhering to viscoelastic support 46 is the abutting surface Sc, and a thin film electrode that is laminated on the main surface adhering to the viscoelastic support 46 is grounded.

In the pickup sensor 100c shown in FIG. 5, the converter film 10 may be the converter film shown in FIG. 1 that is not folded or may be the converter film shown in FIG. 4 that is folded.

Figure 7:
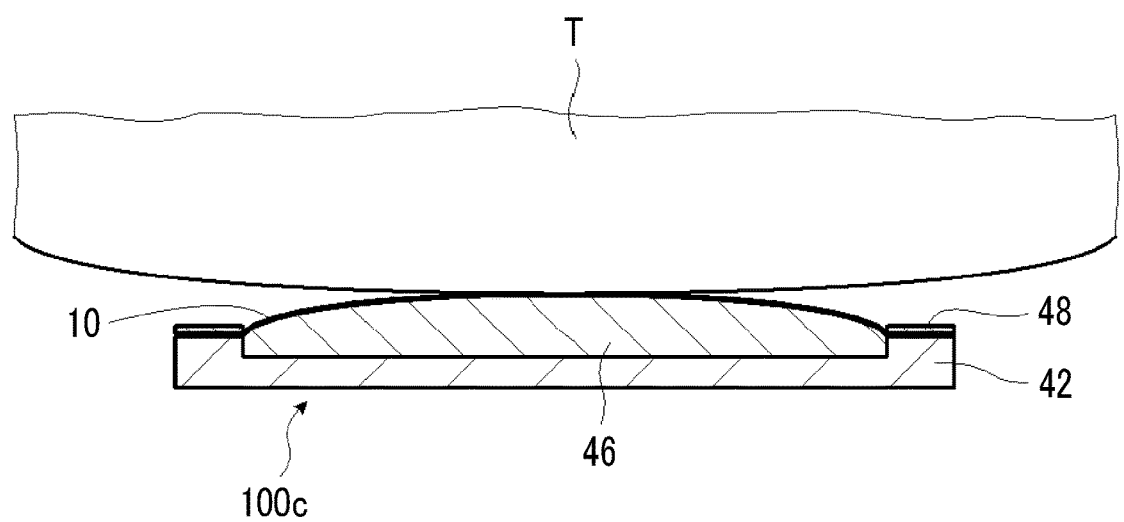
FIG. 7 is a cross-sectional view schematically showing an example where the pickup sensor shown in FIG. 5 is disposed in the test object.

In the converter unit 40, the converter film 10 that is laminated on the thin film electrode is used as a vibration plate on opposite surfaces of a piezoelectric polymer composite in which piezoelectric particles are dispersed in a viscoelastic matrix that is formed of a polymer material having viscoelasticity at normal temperature. The converter unit 40 supports the converter film 10 in a curved state. As shown in FIG. 7, the converter unit 40 is provided to detect vibration in a state where the curved converter film 10 is pressed against the test object T.

The converter film 10 of the converter unit 40 expands or contracts in an in-plane direction according to vibration (sound) transmitted from the test object T such that the vibration (sound) is converted into an electrical signal.

Here, the thin film electrode on the viscoelastic support 46 side is grounded. Therefore, the piezoelectric layer 12 is positioned between the test object T and the grounded thin film electrode. Thus the grounded thin film electrode functions as an electromagnetic shield such that the piezoelectric layer 12 can be prevented from being affected by an external electromagnetic noise.

Since the converter film 10 itself as a vibration plate is thin, the converter unit 40 including the converter film 10 can be reduced in thickness, and thus can be reduced in weight.

In addition, the converter film 10 is curved and held in a case where it is expanded. Therefore, the expansion amount of the converter film 10 according to the vibration of the test object T increases, and micro vibration can be detected with higher sensitivity.

Hereinafter, the converter unit 40 will be described in detail.

The case 42 is a holding member that holds the converter film 10 and the viscoelastic support 46 together with the pressing member 48. The case 42 is formed of plastic, metal, wood, or the like, and has a box shape with one open surface. In the example shown in the drawing, the case 42 has a thin hexahedral shape in which one of the largest surfaces is the open surface. In addition, the open portion has a square shape. The case 42 accommodates the viscoelastic support 46.

In the converter unit, the shape of the case 42 (that is, the shape of the converter unit) is not limited to a quadrangular cylindrical shape and may have various shapes such as a circular cylindrical shape, a quadrangular cylindrical with a rectangular bottom surface, or a cylindrical shape with a polygonal bottom surface.

The viscoelastic support 46 has appropriate viscosity and elasticity, holds the converter film 10 in a curved state, and applies a given mechanical bias to any position of the converter film 10 such that the expansion and contraction movement of the converter film 10 is converted into a forward and backward movement without waste.

In the example shown in the drawing, the viscoelastic support 46 has a quadrangular columnar shape having substantially the same bottom surface shape as the bottom surface of the case 42. In addition, the height of the viscoelastic support 46 is more than the depth of the case 42.

A material of the viscoelastic support 46 is not particularly limited as long as it has appropriate viscosity and elasticity, does not interfere vibration of the piezoelectric film, and is suitably deformable. Examples of the material of the viscoelastic support 46 include non-woven fabric such as wool felt or wool felt including rayon or PET, a foamed material (foamed plastic) such as glass wool or polyurethane, polyester wool, a laminate of a plurality of sheets of paper, a magnetic fluid, and a paint.

The specific gravity of the viscoelastic support 46 is not particularly limited and may be appropriately selected according to the kind of the viscoelastic support. For example, in a case where the viscoelastic support is formed of felt, the specific gravity is preferably 50 to 500 kg/m$^3$ and more preferably 100 to 300 kg/m$^3$. In a case where the viscoelastic support is formed of glass wool, the specific gravity is preferably 10 to 100 kg/m$^3$.

The pressing member 48 is provided to support the converter film 10 in a state where the converter film 10 is pressed against the viscoelastic support 46, and is a plate-shaped member that is formed of plastic, metal, wood, or the like and has a square shape having an opening at the center. The pressing member 48 has the same shape as the open surface of the case 42, and the opening of the pressing member 48 has a square shape that is the same as the shape of the open portion of the case 42.

In the converter unit 40, the viscoelastic support 46 is accommodated in the case 42, the case 42 and the viscoelastic support 46 are covered with the converter film 10, and the periphery of the converter film 10 is brought into contact with the open surface of the case 42 by the pressing member 48. In this state, the pressing member 48 is fixed to the case 42. This way, the converter unit 40 is configured.

A method of fixing the pressing member 48 to the case 42 is not particularly limited, and various well-known methods such as a method using a screw or using a bolt and a nut or a method using a holding device for fixing can be used.

In the converter unit 40, the height (thickness) of viscoelastic support 46 is more than the height of an inner surface of the case 42. That is, before fixing the converter film 10 and the pressing member 48, the viscoelastic support 46 protrudes from an upper surface of the case 42.

Therefore, in the converter unit 40, the viscoelastic support 46 is held in a state where the viscoelastic support 46 is pressed down toward a peripheral portion of the viscoelastic support 46 by the converter film 10 such that the thickness thereof is small. That is, the converter film 10 is held in a state where at least a part of the main surfaces of the converter film 10 is curved.

At this time, it is preferable that the entire surface of the viscoelastic support 46 is pressed in a plane direction of the converter film 10 such that the thickness is thin over the entire surface. That is, it is preferable that the entire surface of the converter film 10 is supported by being pressed by the viscoelastic support 46.

In addition, it is preferable that a curvature of the curved portion formed as described above changes gradually from the center toward the peripheral portion. As a result, the resonance frequency is dispersed such that the frequency band thereof can be widened.

In addition, in the converter unit 40, the viscoelastic support 46 is compressed in a thickness direction toward the pressing member 48. Due to a static viscoelastic effect (stress relaxation), a given mechanical bias can be maintained at any position of the converter film 10. As a result, the expansion and contraction movement of the converter film 10 is converted into a forward and backward movement without waste. Therefore, the planar converter unit 40 that is thin, can obtain a sufficient sound volume, and has excellent acoustic characteristics can be obtained.

In the converter unit 40 having the above-described configuration, a region of the converter film 10 corresponding to the opening of the pressing member 48 is a region that actually vibrates. That is, the pressing member 48 is a portion that defines the vibration region. Accordingly, the size of the vibration region relative to the size of the entire converter unit 40 can be easily increased, and thus the size of the converter unit 40 can be easily reduced.

In addition, it is preferable that the surface of the converter unit 40 on the converter film 10 side is similar to the vibration region. That is, it is preferable that the external shape of the pressing member 48 is similar to the shape of the opening.

In addition, in a case where seen from a direction perpendicular to the main surfaces of the converter film 10, the shape of the vibration region is not particularly limited to a quadrangular shape and may be a polygonal shape or a circular shape. That is, an opening 48a of the pressing member 48 may have various shapes such as a quadrangular shape, a polygonal shape, or a circular shape.

In the converter unit 40, a pressing pressure under which the viscoelastic support 46 is pressed by the converter film 10 is not particularly limited. A surface pressure at a position where the surface pressure is low is 0.005 MPa to 1.0 MPa and preferably about 0.02 MPa to 0.2 MPa.

Further, the thickness of the viscoelastic support 46 is not particularly limited, and the thickness before pressing is 1 mm to 100 mm and preferably 10 mm to 50 mm.

In addition, in the example shown in the drawing, the viscoelastic support 46 having viscoelasticity is used. However, the embodiment is not limited to this configuration, and an elastic support having at least elasticity may be used.

For example, an elastic support having elasticity may be provided instead of the viscoelastic support 46.

Examples of the elastic support include natural rubber or various synthetic rubbers.

Here, in the converter unit 40 of the pickup sensor 100c shown in FIG. 5, the entire peripheral region of the converter film 10 is pressed against the case 42 by the pressing member 48, but the embodiment of the present invention is not limited thereto.

That is, in the converter unit including the converter film 10, the converter film 10 may be pressed/fixed to four corners of the upper surface of the case 42 by using, for example, a screw, a bolt and a nut, or a holding device instead of providing the pressing member 48.

In addition, an O-ring or the like may be interposed between the case 42 and the converter film 10. With the above-described configuration, a damper effect can be exhibited, vibration of the converter film 10 can be prevented from being transmitted to the case 42, and higher acoustic characteristics can be obtained.

In addition, the converter unit including the converter film 10 may not include the case 42 that accommodates the viscoelastic support 46.

For example, the following configuration can also be used. A viscoelastic support is placed on a support plate having rigidity, the converter film 10 is placed to cover the viscoelastic support, and the above-described pressing member is placed on the peripheral portion. Next, the pressing member is fixed to the support plate using a screw or the like such that the viscoelastic support is pressed together with the pressing member.

The size of the support plate may be more than that of the viscoelastic support. Further, as a material of the support plate, various vibration plates of polystyrene, foamed PET, or carbon fibers can be used.

Further, the embodiment is not limited to the configuration where the periphery of the converter unit is pressed. For example, the center of a laminate including the viscoelastic support 46 and the converter film 10 may also be pressed by any means.

That is, various configurations can be adopted as long as the converter unit is held in a state where the converter film 10 is curved.

Alternatively, the converter film 10 may be bonded to a resin film to impart tension (to be curved). By holding the converter film 10 in a curved state using the resin film, a flexible speaker can be obtained.

Alternatively, the converter film 10 may be stretched over a curved frame.

In addition, in the example shown in FIG. 5, the converter film 10 is supported by being pressed against the viscoelastic support 46 using the pressing member 48, but the embodiment is not limited thereto. For example, using the converter film 10 having a larger size than the opening surface of the case 42, an end portion of the converter film 10 may be fixed to a back surface side of the case 42. That is, by covering the case 42 and the viscoelastic support 46 disposed inside the case 42 with the converter film 10 having a large size than the opening surface of the case 42 and pulling the end portion of the converter film 10 toward the back surface side of the case 42, the converter film 10 may be pressed against the viscoelastic support 46 to imparted with tension to be curved, and the end portion of the converter film may be fixed to the back surface side of the case 42.

Alternatively, an airtight case may be used, an open end of the case may be covered with the converter film to be sealed, gas may be introduced into the case to apply pressure to the converter film, and the converter film may be held in a state where it is expanded in a convex shape.

In addition, in the converter unit 40 shown in FIG. 5, the converter film 10 is pressed by the viscoelastic support 46 and is held in a state where the main surfaces are curved in a convex shape. However, the embodiment is not limited to the configuration where the converter film 10 is held in a curved state.

For example, a convex portion may be formed in the converter film 10 itself such that the converter film 10 is curved. A method of forming the convex portion is not particularly limited, and various well-known methods of processing a resin film can be used. For example, the convex portion may be formed using a forming method such as a vacuum compression molding method or embossing.

Here, the pickup sensor according to the embodiment of the present invention may include a suction cup member in addition to the converter unit.

Figure 8:
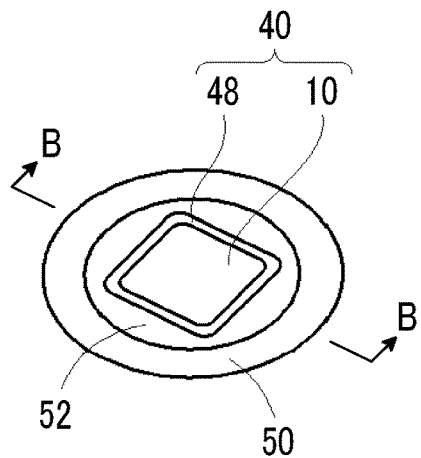
FIG. 8 is a perspective view schematically showing still another example of the pickup sensor according to the present invention.
Figure 9:
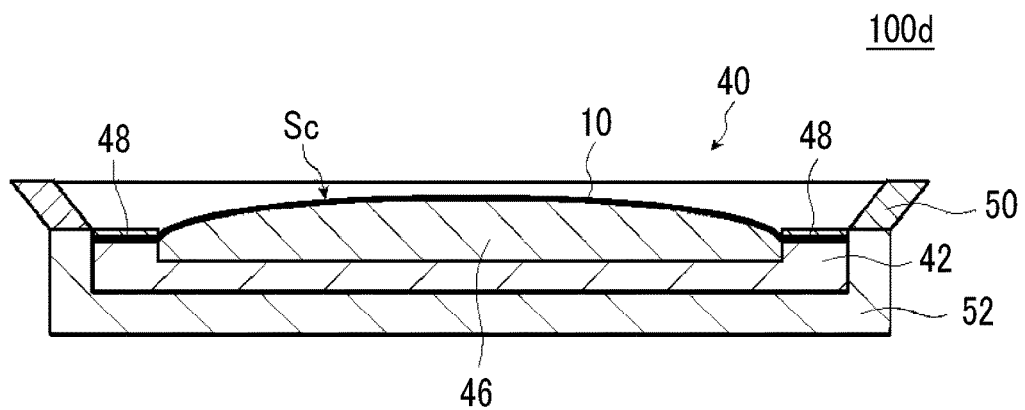
FIG. 9 is a cross-sectional view taken along line B-B of the pickup sensor shown in FIG. 8.

FIG. 8 is a perspective view schematically showing still another example of the pickup sensor according to the embodiment of the present invention. FIG. 9 is a cross-sectional view taken along line B-B of the pickup sensor shown in FIG. 8.

A pickup sensor 100d shown in FIGS. 8 and 9 includes: the same converter unit 40 as that of the pickup sensor 100c shown in FIG. 5; a second case 50 in which the converter unit 40 is placed; and a suction cup member 52 that is attached to the second case 50.

The second case 50 is formed of plastic, metal, wood, or the like, and has a box shape with one open surface. In the example shown in the drawing, the second case 50 has a thin bottomed cylindrical shape in which one of circular surfaces is the open surface. In addition, the open portion has a rectangular shape, has substantially the same size as the largest surface of the case 42 of the converter unit 40, and has a depth that is substantially the same as the total thickness of the case 42 and the pressing member 48.

As shown in FIG. 9, the second case 50 accommodates the converter unit 40 such that the converter film 10 faces outside.

The suction cup member 52 is formed of an elastomer, a rubber, a silicon, or other elastic materials, is a well-known suction cup member of the related art that adsorbs to an attachment target (test object T) using a difference in atmospheric pressure in a state where a gap between the suction cup member and the attachment target is made to be substantially in a vacuum, is disposed on an edge portion of the open surface of the second case 50.

Accordingly, the converter unit 40 is disposed substantially at the center of an adsorption surface (surface abutting against the test object T) of the suction cup member 52.

Figure 10:
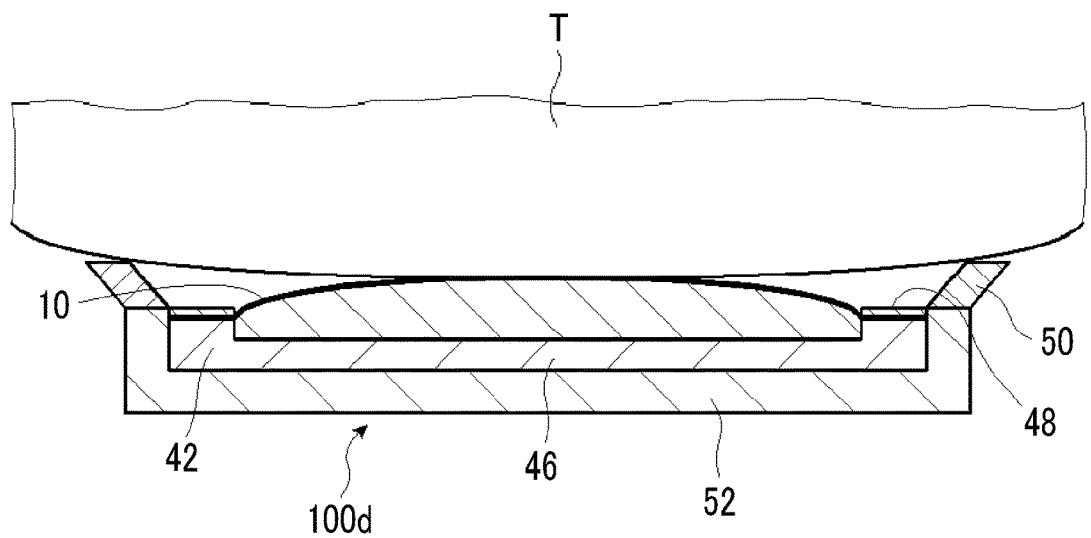
FIG. 10 is a cross-sectional view schematically showing an example where the pickup sensor shown in FIG. 8 is disposed in the test object.

The pickup sensor 100d includes the suction cup member 52, and the pickup sensor 100d is attached to the test object T by the suction cup member 52 as shown in FIG. 10 such that the converter film 10 is made to abut against the test object T. As a result, the pickup sensor 100d is not likely to be tilted and can be stably fixed.

Figure 11:
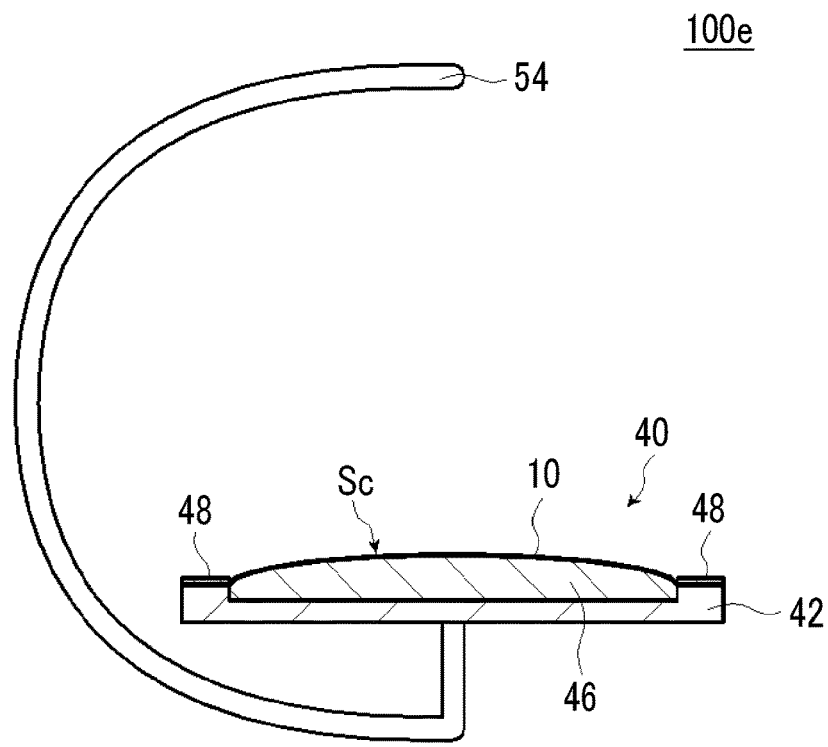
FIG. 11 is a cross-sectional view schematically showing still another example of the pickup sensor according to the present invention.

Further, as in the case of a pickup sensor 100e shown in FIG. 11, a holding member 54 having elasticity that is formed in a substantially C-shape may be provided such that the holding member 54 presses and holds the converter film 10 (converter unit 40) against the test object T.

The holding member 54 is an elastic wire rod (including a round bar or a band plate) having a substantially C-shape corresponding to the shape of an attachment position of the pickup sensor. A material of the holding member 54 may be metal or a synthetic resin.

The converter unit 40 is disposed at one end portion of the holding member 54, and is connected to a surface of the converter unit 40 opposite to the converter film 10.

For example, in a case where the pickup sensor 100e is used as a throat microphone, the holding member 54 is a member (so-called neck band) having a substantially C-shape and a size that can be worn around a neck of a human body. Opposite end portions of the holding member 54 bias the test object T and the converter unit 40 inward such that the test object T and the converter film 10 of the converter unit 40 are held to adhere to each other.

In a case where the pickup sensor is attached to the test object T using a tape or the like, a portion of the test object T that is attached by the tape or the like is fixed. As a result, vibration is not likely to be transmitted through the inside of the test object T, and vibration transmitted to the pickup sensor (converter film) may be small.

On the other hand, by providing the holding member 54 as described above, a portion of the test object T to which the pickup sensor is attached can be prevented from being fixed, and vibration can be reliably transmitted through the inside of the test object T. Therefore, the pickup sensor (converter film) can more reliably detect vibration.

Figure 12:
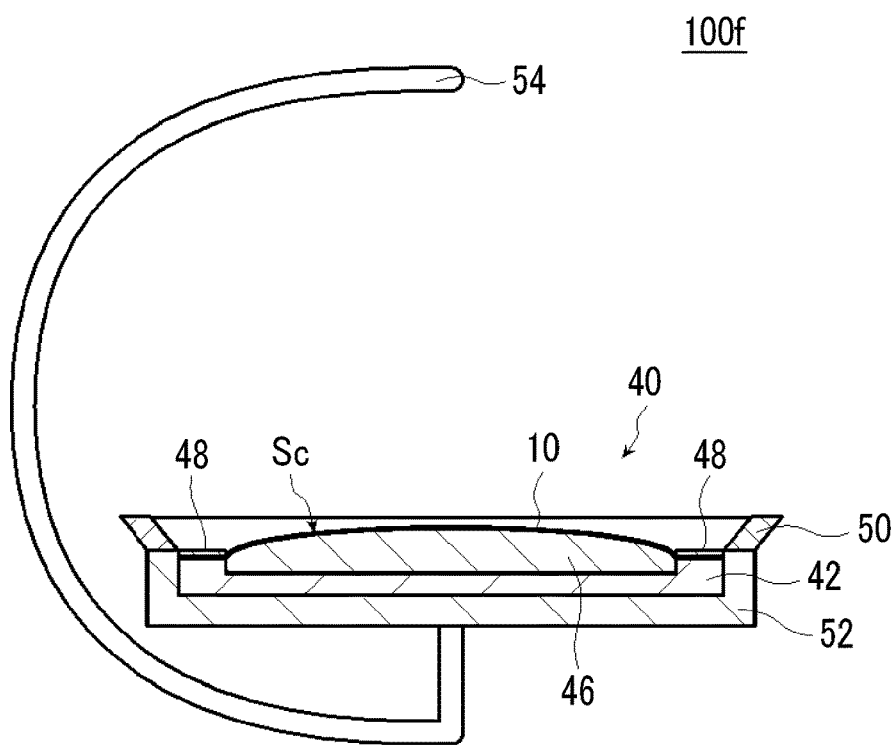
FIG. 12 is a cross-sectional view schematically showing still another example of the pickup sensor according to the present invention.

In addition, as in the case of a pickup sensor 100f shown in FIG. 12, the suction cup member 52 and the holding member 54 may be provided.

Next, the converter film 10 used in the pickup sensor according to the embodiment of the present invention will be described.

As described above, the converter film 10 includes: a piezoelectric layer 12 that is a sheet-like material having piezoelectricity; the lower thin film electrode 14 that is laminated on one surface of the piezoelectric layer 12; a lower protective layer 18 that is laminated on the lower thin film electrode 14; an upper thin film electrode 16 that is laminated on another surface of the piezoelectric layer 12; and an upper protective layer 20 that is laminated on the upper thin film electrode 16.

Here, it is preferable that the piezoelectric polymer composite (piezoelectric layer 12) satisfies the following requirements.

(i) Flexibility

For example, in a case where the piezoelectric polymer composite is gripped as a portable apparatus in a gently bent state as with documents such as a newspaper or a magazine, the piezoelectric polymer composite continuously undergoes significant bending deformation at a relatively low frequency of several Hz or lower due to external conditions. At this time, in a case where the piezoelectric polymer composite is hard, bending stress corresponding to the hardness is generated, and an interface between the polymer matrix and the piezoelectric particles cracks, which may lead to fracture. Accordingly, appropriate flexibility is required in the piezoelectric polymer composite. In addition, as strain energy can be diffused to the outside as heat, the stress can be relaxed. Accordingly, it is required that the loss tangent of the piezoelectric polymer composite is appropriately large.

(ii) Sound Quality

In the pickup sensor used as a throat microphone, a biological sensor, or a sensor for a device, it is preferable that vibration is detected in an audible frequency of 20 Hz to 10 kHz Accordingly, in order to improve the transmission efficiency of vibration energy, the piezoelectric polymer composite requires an appropriate hardness. In addition, in a case where frequency characteristics of the pickup sensor are smooth, when a minimum resonance frequency $f_0$ varies depending on a variation in curvature, a variation of sound quality also decreases. Accordingly, it is required that the loss tangent of the piezoelectric polymer composite is appropriately large.

Based on the above-described points, it is required that the piezoelectric polymer composite of the converter film used in the pickup sensor is hard with respect to vibration at 20 Hz to 10 kHz and is flexible with respect to vibration at several Hz or lower. In addition, it is required that the loss tangent of the piezoelectric polymer composite is appropriately large with respect to vibration in all the frequencies of 10 kHz or lower.

In general, a polymer solid has a viscoelastic relaxation mechanism, and along with an increase in temperature or a decrease in frequency, a large-scale molecular motion is observed as a decrease (relaxation) in storage elastic modulus (Young's modulus) or a maximum value (absorption) of loss elastic modulus. In particular, relaxation caused by micro-Brownian motion of a molecular chain in an amorphous region is called primary dispersion and is observed as an extremely large relaxation. A temperature at which the primary dispersion occurs is a glass transition point (Tg), and the viscoelastic relaxation mechanism is most significant at this temperature.

In the piezoelectric polymer composite (piezoelectric layer 12), the polymer material having a glass transition point at normal temperature, in other words, the polymer material having viscoelasticity at normal temperature is used as the matrix. As a result, the piezoelectric polymer composite which is hard with respect to vibration at 20 Hz to 10 kHz and is flexible with respect to vibration of several Hz or lower can be realized. In particular, from the viewpoint of, for example, suitably exhibiting the hardness and the flexibility, it is preferable that a polymer material having a glass transition temperature at a frequency of 1 Hz at normal temperature, that is, 0° C. to 50° C. is used as the matrix of the piezoelectric polymer composite.

As the polymer material having viscoelasticity at normal temperature, various well-known materials can be used. It is preferable that a polymer material has a maximum value of loss tangent Tan δ of 0.5 or higher at a frequency of 1 Hz at normal temperature, that is, 0° C. to 50° C. in a dynamic viscoelasticity test.

As a result, in a case where the piezoelectric polymer composite is gently bent by external force, stress concentration on an interface between the polymer matrix and the piezoelectric particles in a maximum bending moment portion is relaxed, and high flexibility can be expected.

In addition, it is preferable that the storage elastic modulus (E') of the polymer material at a frequency of 1 Hz in dynamic viscoelasticity measurement is 100 MPa or higher at 0° C. and is 10 MPa or lower at 50° C.

As a result, the bending moment generated in a case where the piezoelectric polymer composite is gently bent by external force can be reduced, and concurrently, the piezoelectric polymer composite can be made to be hard with respect to acoustic vibration of 20 Hz to 10 kHz.

In addition, it is more preferable that the polymer material has a relative dielectric constant of 10 or higher at 25° C. As a result, in a case where a voltage is applied to the piezoelectric polymer composite, a higher electric field is applied to the piezoelectric particles in the polymer matrix. Therefore, a large amount of deformation can be expected.

However, on the other hand, in consideration of, for example, securing satisfactory moisture resistance, it is also suitable that the relative dielectric constant of the polymer material at 25° C. is 10 or lower.

Examples of the polymer material satisfying the above-described conditions include cyanoethylated polyvinyl alcohol (cyanoethylated PVA), polyvinyl acetate, polyvinylidene chloride-co-acrylonitrile, a polystyrene-vinyl polyisoprene block copolymer, polyvinyl methyl ketone, and polybutyl methacrylate. In addition, as the polymer material, a commercially available product such as HYBRAR 5127 (manufactured by Kuraray Co., Ltd.) can be preferably used. Among these, a material having a cyanoethyl group is preferably used, and a cyanoethylated PVA is more preferably used.

Among these polymer materials, one kind may be used alone, or a combination (mixture) of plural kinds may be used.

The viscoelastic matrix 24 that is formed of the polymer material having viscoelasticity at normal temperature is optionally used in combination with a plurality of polymer materials.

That is, for example, in order to adjust dielectric characteristics or mechanical characteristics, optionally, not only a viscoelastic material such as cyanoethylated PVA but also other dielectric polymer materials are added to the viscoelastic matrix 24.

Examples of the dielectric polymer materials which can be added include: fluorine polymers such as polyvinylidene fluoride, vinylidene fluoride-tetrafluoroethylene copolymers, vinylidene fluoride-trifluoroethylene copolymers, polyvinylidene fluoride-trifluoroethylene copolymers, and polyvinylidene fluoride-tetrafluoroethylene copolymers; polymers having a cyano group or a cyanoethyl group such as vinylidene cyanide-vinyl acetate copolymers, cyanoethyl cellulose, cyanoethyl hydroxysaccharose, cyanoethyl hydroxycellulose, cyanoethyl hydroxypullulan, cyanoethyl methacrylate, cyanoethyl acrylate, cyanoethyl hydroxyethyl cellulose, cyanoethyl amylose, cyanoethyl hydroxypropyl cellulose, cyanoethyl dihydroxypropyl cellulose, cyanoethyl hydroxypropyl amylose, cyanoethyl polyacrylamide, cyanoethyl polyacrylate, cyanoethyl pullulan, cyanoethyl polyhydroxymethylene, cyanoethyl glycidol pullulan, cyanoethyl saccharose, and cyanoethyl sorbitol; and synthetic rubbers such as nitrile rubber and chloroprene rubber.

Among these, a polymer material having a cyanoethyl group is preferably used.

As a dielectric polymer which is added to the viscoelastic matrix 24 of the piezoelectric layer 12 in addition to the material having viscoelasticity at normal temperature such as cyanoethylated PVA, one kind may be used alone, or plural kinds may be used.

In addition, in addition to the dielectric polymer, a thermoplastic resin such as a vinyl chloride resin, polyethylene, polystyrene, a methacrylic resin, polybutene, or isobutylene; or a thermosetting resin such as a phenol resin, a urea resin, a melamine resin, an alkyd resin, or mica may be added in order to adjust the glass transition temperature Tg.

Further, in order to improve viscosity, a viscosity imparting agent such as rosin ester, rosin, terpene, terpene phenol, or a petroleum resin may be added.

In the viscoelastic matrix 24 of the piezoelectric layer 12, the addition amount of polymers other than the viscoelastic material such as cyanoethylated PVA is not particularly limited, but the proportion thereof in the viscoelastic matrix 24 is preferably 30 wt % or lower.

As a result, the characteristics of the polymer material added can be exhibited without deterioration in the viscoelastic relaxation mechanism of the viscoelastic matrix 24. Therefore, the preferable results can be obtained from the viewpoint of, for example, obtaining high dielectric constant, improving heat resistance, and improving adhesiveness between the piezoelectric particles 26 and an electrode layer.

In addition, in order to improve the dielectric constant of the piezoelectric layer 12, dielectric particles may be added to the viscoelastic matrix 24.

The dielectric particles are particles having a high relative dielectric constant of 80 or higher at 25° C.

Examples of the dielectric particles include lead zirconate titanate (PZT), barium titanate (BaTiO$_3$), titanium oxide (TiO$_2$), strontium titanate (SrTiO$_3$), lead lanthanum zirconate titanate (PLZT), zinc oxide (ZnO), and a solid solution (BFBT) of barium titanate and bismuth ferrite (BiFeO$_3$). Among these, from the viewpoint of a high relative dielectric constant, barium titanate (BaTiO$_3$) is preferably used as the dielectric particles.

The average particle size of the dielectric particles is preferably 0.5 μm or less.

In addition, a volume fraction of the dielectric particles with respect to the total volume of the viscoelastic matrix and the dielectric particles is preferably 5% to 45%, more preferably 10% to 30%, and still more preferably 20% to 30%.

The piezoelectric particles 26 are formed of ceramic particles having a perovskite crystal structure or a wurtzite crystal structure.

Examples of the ceramic particles constituting the piezoelectric particles 26 include particles of lead zirconate titanate (PZT), lead lanthanum zirconate titanate (PLZT), barium titanate (BaTiO$_3$), zinc oxide (ZnO), a solid solution (BFBT) of barium titanate and bismuth ferrite (BiFe$_3$), and the like.

Among these ceramic particles, one kind may be used alone, or a combination (mixture) of plural kinds may be used.

The particle size of the piezoelectric particles 26 may be appropriately selected according to the size and use of the converter film 10 and is preferably 1 to 10 μm according to the investigation by the present inventors.

By adjusting the particle size of the piezoelectric particles 26 to be in the above-described range, the preferable results can be obtained from the viewpoint that voltage resistance can be improved such that high piezoelectric characteristics and flexibility can be simultaneously realized.

In FIG. 2, the piezoelectric particles 26 in the piezoelectric layer 12 are dispersed in the viscoelastic matrix 24 with uniformity and regularity, but the embodiment of the present invention is not limited thereto.

That is, the piezoelectric particles 26 in the piezoelectric layer 12 may be irregularly dispersed in the viscoelastic matrix 24 as long as they are preferably uniformly dispersed.

A ratio of the amount of the viscoelastic matrix 24 to the amount of the piezoelectric particles 26 in the piezoelectric layer 12 of the converter film 10 may be appropriately set according to the size of the converter film 10 in the plane direction, the thickness of the converter film 10, the use of the converter film 10, characteristics required for the converter film 10, and the like.

Here, according to the investigation by the present inventors, the volume fraction of the piezoelectric particles 26 in the piezoelectric layer 12 is preferably 30% to 70%, more preferably 50% or higher, and still more preferably 50% to 70%.

By adjusting the ratio of the amount of the viscoelastic matrix 24 to the amount of the piezoelectric particles 26 to be in the above-described range, the preferable results can be obtained from the viewpoint that, for example, high piezoelectric characteristics and flexibility can be simultaneously realized.

In addition, in the converter film 10, the thickness of the piezoelectric layer 12 is also not particularly limited, and may be appropriately set according to the size of the converter film 10, the use of the converter film 10, characteristics required for the converter film 10, and the like.

Here, according to the investigation by the present inventors, bending caused by the weight can be reduced by reducing the thickness of the piezoelectric layer 12. In addition, by reducing the weight of the piezoelectric layer 12, the followability of the piezoelectric film with respect to an applied voltage is improved such that the sound pressure or sound quality can be improved. In addition, flexibility can be imparted. On the other hand, in a case where the thickness of the piezoelectric layer 12 is extremely small, local short-circuiting may occur regarding rigidity during continuous application of a voltage or during application of a high voltage. In addition, the rigidity may deteriorate.

From the above-described viewpoint, the thickness of the piezoelectric layer 12 is preferably 5 μm to 100 μm, more preferably 8 μm to 50 μm, still more preferably 10 to 40 μm, and even still more preferably 15 to 25 μm.

It is preferable that the piezoelectric layer 12 undergoes polling. The polling will be described below in detail.

As shown in FIG. 2, in the converter film 10, the lower thin film electrode 14 is formed on one surface of the piezoelectric layer 12, the lower protective layer 18 is formed on the lower thin film electrode 14, the upper thin film electrode 16 is formed on another surface of the piezoelectric layer 12, and the upper protective layer 20 is formed on the upper thin film electrode 16. Here, the upper thin film electrode 16 and the lower thin film electrode 14 form a pair of electrodes.

In addition to the above-described layers, the converter film 10 includes, for example, electrode extraction portions that extract electrodes from the upper thin film electrode 16 and the lower thin film electrode 14, and an insulating layer that covers a region where the piezoelectric layer 12 is exposed and prevents short-circuiting and the like.

As the electrode extraction portion, a portion where the thin film electrode and the protective layer protrude in a convex shape to the outside in the plane direction of the piezoelectric layer may be provided. Alternatively, the electrode extraction portion may be provided by removing a part of the protective layer to form a hole portion and inserting a conductive material such as silver paste into the hole portion such that the conductive material and the thin film electrode are electrically connected.

In each of the thin film electrodes, the number of electrode extraction portions is not limited to one and may be two or more. In particular, in a case where the electrode extraction portion is provided by removing a part of the protective layer and inserting the conductive material into the hole portion, the number of electrode extraction portions is preferably three or more in order to more reliably secure electric connection.

In the converter film 10, opposite surfaces of the piezoelectric layer 12 are interposed between the pair of electrodes, that is, between the upper thin film electrode 16 and the lower thin film electrode 14, and this laminate is interposed between the upper protective layer 20 and the lower protective layer 18.

By expanding and contracting a region interposed between the upper thin film electrode 16 and the lower thin film electrode 14, a voltage is generated between the upper thin film electrode 16 and the lower thin film electrode 14.

In the converter film 10, the upper protective layer 20 and the lower protective layer 18 have a function of covering the upper thin film electrode 16 and the lower thin film electrode 14 to impart appropriate rigidity and mechanical strength to the piezoelectric layer 12. That is, the piezoelectric layer 12 including the viscoelastic matrix 24 and the piezoelectric particles 26 may exhibit extremely high flexibility with respect to gentle bending deformation and may exhibit insufficient rigidity or mechanical strength depending on the use. In the converter film 10, the upper protective layer 20 and the lower protective layer 18 are provided in order to compensate for the insufficient rigidity or mechanical strength.

The lower protective layer 18 and the upper protective layer 20 have the same configuration except for different disposition positions. Therefore, in the following description, in a case where it is not necessary to distinguish the lower protective layer 18 and the upper protective layer 20 from each other, the two members will also be collectively referred to as "protective layer".

The upper protective layer 20 and the lower protective layer 18 are not particularly limited, and various sheet-like materials can be used. For example, various resin films are preferable. Among these, for example, from the viewpoint of obtaining excellent mechanical properties and heat resistance, polyethylene terephthalate (PET), polypropylene (PP), polystyrene (PS), polycarbonate (PC), polyphenylene sulfite (PPS), polymethyl methacrylate (PMMA), polyether imide (PEI), polyimide (PI), polyamide (PA, aramid), polyethylene naphthalate (PEN), triacetyl cellulose (TAC), or a cyclic olefin resin is preferably used.

Among these, for example, from the viewpoint of exhibiting excellent heat resistance at a glass transition temperature Tg of 150° C. or higher, polyamide, polyimide, polyether imide, polycarbonate, or triacetyl cellulose is preferably used. As a result, the external appearance can be prevented from being damaged by heat generation during voltage application, and a shelf test and a driving test at a high temperature can be endured.

The thicknesses of the upper protective layer 20 and the lower protective layer 18 are not particularly limited. In addition, the thicknesses of the upper protective layer 20 and the lower protective layer 18 are basically the same but may be different from each other.

Here, in a case where the rigidity of the upper protective layer 20 and the lower protective layer 18 is excessively high, the expansion and contraction of the piezoelectric layer 12 is limited, and the flexibility also deteriorates. Therefore, unless excellent mechanical strength and handleability as a sheet-like material are required, it is preferable that the thicknesses of the upper protective layer 20 and the lower protective layer 18 are as small as possible.

According to the investigation by the present inventors, in a case where the thicknesses of the upper protective layer 20 and the lower protective layer 18 are two times or more the thickness of the piezoelectric layer 12, the preferable results can be obtained from the viewpoints of, for example, securing rigidity and obtaining an appropriate flexibility.

For example, in a case where the thickness of the piezoelectric layer 12 is 20 μm and the upper protective layer 20 and the lower protective layer 18 are formed of PET, the thicknesses of the upper protective layer 20 and the lower protective layer 18 are preferably 40 or less, more preferably 20 μm or less, and still more preferably 15 μm or less.

In the converter film 10, the upper thin film electrode (hereinafter, also referred to as "upper electrode") 16 is formed between the piezoelectric layer 12 and the upper protective layer 20, and the lower thin film electrode (hereinafter, also referred to as "lower electrode" 14 is formed between the piezoelectric layer 12 and the lower protective layer 18.

An upper electrode 16 and a lower electrode 14 are provided in order to detect a voltage generated from the piezoelectric layer 12 along with the expansion and contraction of the converter film 10.

The lower electrode 14 and the upper electrode 16 have the same configuration except for different sizes and different disposition positions. Therefore, in the following description, in a case where it is not necessary to distinguish the lower electrode 14 and the upper electrode 16 from each other, the two members will also be collectively referred to as "thin film electrode".

In the embodiment of the present invention, a material for forming the upper electrode 16 and the lower electrode 14 is not particularly limited, and various conductors can be used. Specific example of the material for forming the upper electrode 16 and the lower electrode 14 include carbon, palladium, iron, tin, aluminum, nickel, platinum, gold, silver, copper, chromium, molybdenum, alloys thereof, and indium tin oxide. Among these, for example, any one of copper, aluminum, gold, silver, platinum, or indium tin oxide is preferable.

In addition, a method of forming the upper electrode 16 and the lower electrode 14 is not particularly limited, and various well-known methods such as a vapor phase deposition method (vacuum deposition method) such as vacuum deposition or sputtering, a film forming method using plating, or a method of bonding a foil formed of the above-described material can be used.

In particular, from the viewpoint of securing the flexibility of the converter film 10, a copper thin film or an aluminum thin film that is formed by vacuum deposition is preferably used as the upper electrode 16 and the lower electrode 14. In particular, a copper thin film that is formed by vacuum deposition is more preferably used.

The thicknesses of the upper electrode 16 and the lower electrode 14 are not particularly limited. In addition, the thicknesses of the upper electrode 16 and the lower electrode 14 are basically the same but may be different from each other.

Here, as in the case of the upper protective layer 20 and the lower protective layer 18, in a case where the rigidity of the upper electrode 16 and the lower electrode 14 is excessively high, the expansion and contraction of the piezoelectric layer 12 is limited, and the flexibility also deteriorates. Therefore, in a case where the electrical resistance of the upper electrode 16 and the lower electrode 14 is not excessively high, it is preferable that the upper electrode 16 and the lower electrode 14 are as thin as possible.

Here, according to the investigation by the present inventors, in a case where the product of the thickness and the Young's modulus of each of the upper electrode 16 and the lower electrode 14 is lower than the product of the thickness and the Young's modulus of each of the upper protective layer 20 and the lower protective layer 18, the flexibility does not significantly deteriorate, which is preferable.

For example, in a case where the upper protective layer 20 and the lower protective layer 18 formed of PET (Young's modulus: about 6.2 GPa) are used in combination with the upper electrode 16 and the lower electrode 14 formed of copper (Young's modulus: about 130 GPa), assuming that the thickness of each of the upper protective layer 20 and the lower protective layer 18 is 25 μm, the thickness of each of the upper electrode 16 and the lower electrode 14 is 1.2 μm or less, more preferably 0.3 μm, and still more preferably 0.1 μm or less.

In addition, it is not necessary that the thin film electrode is formed corresponding to the entire surface of the piezoelectric layer 12 (the lower protective layer 18 and/or the upper protective layer 20).

That is, at least one thin film electrode may be smaller than, for example, the piezoelectric layer 12, and the piezoelectric layer 12 and the protective layer may come into direct contact with each other in the peripheral portion of the converter film 10.

Alternatively, it is not necessary that the protective layer including the thin film electrode formed on the entire surface is formed corresponding to the entire surface of the piezoelectric layer 12. In this case, the second protective layer in direct contact with the piezoelectric layer 12 may be separately provided on the surface side of the protective layer.

In addition, a coating layer may be further provided between the thin film electrode and the piezoelectric layer 12 in order to improve, for example, adhesive strength or flexibility. In this case, the coating layer may be formed on any one of the thin film electrode or the piezoelectric layer 12.

In this case as the polymer component, a thermoplastic resin such as poly(meth)acryl, polyurethane, polyester, polyolefin, PVA, or polystyrene, or a thermosetting resin such as a phenol resin or a melamine resin can be used. Among these, a dielectric polymer is preferably used in order to improve acoustic performance. Specifically, for example, the above-described polymer can be preferably used. In addition to the polymer component, high dielectric particles, an antistatic agent, a surfactant, a thickener, or a crosslinking agent may be added.

In addition, in the example shown in the drawing, the layer configuration of the converter film 10 includes: the piezoelectric layer 12; the lower thin film electrode 14 that is laminated on one surface of the piezoelectric layer 12; the lower protective layer 18 that is laminated on the lower thin film electrode 14; the upper thin film electrode 16 that is laminated on another surface of the piezoelectric layer 12; and the upper protective layer 20 that is laminated on the upper thin film electrode 16. However, the embodiment is not limited to this configuration. In addition to the above-described layers, for example, an insulating layer that covers a region where the piezoelectric layer 12 is exposed and prevents short-circuiting or the like, or a colored layer that covers the thin film electrode may be further provided.

For example, a layer configuration including the colored layer may include: the piezoelectric layer 12; the lower thin film electrode 14 that is laminated on one surface of the piezoelectric layer 12; a lower colored layer that is laminated on the lower thin film electrode 14; the lower protective layer 18 that is laminated on the lower colored layer; the upper thin film electrode 16 that is laminated on another surface of the piezoelectric layer 12; an upper colored layer that is laminated on the upper thin film electrode 16; and the upper protective layer 20 that is laminated on the upper colored layer.

By providing the colored layers, rust of the upper thin film electrode 16 and the lower thin film electrode 14 can be made invisible to the outside.

From the viewpoint of making the rust of thin film electrode invisible to the outside, a transmission density of the colored layer is preferably 0.3 or higher and more preferably 0.5 or higher.

The transmission density refers to an optical density measured as a ratio of transmitted light to incidence light. A transmission density of 0.3 corresponds to a transmittance of about 50%, and a transmission density of 0.5 corresponds to a transmittance of about 30%.

In addition, the thickness of the colored layer is preferably 1 µm or less, more preferably 100 nm or less, and still more preferably 40 nm or less.

In addition, an electrical resistivity of the colored layer is preferably as low as possible and is preferably $1\times10^{-7}$ Ωm or lower.

A material for forming the colored layer is not particularly limited as long as it satisfies the above-described transmission density and is not discolored by rust or the like.

Specific examples of the material for forming the colored layer include: a metal such as indium, nickel, titanium, aluminum, gold, platinum, or chromium; an inorganic pigment such as carbon black (CB), titanium oxide, zinc oxide, or barium sulfate; an organic pigment such as a quinacridone pigment, an azo pigment, a benzimidazolone pigment, a phthalocyanine pigment, or an anthraquinone pigment; and a member having light scattering properties that has pores.

From the viewpoints of the transmission density, the thickness, and the electrical resistivity described above, as the material for forming the colored layer, a metal is preferable, and nickel is more preferable.

In addition, a method of forming the colored layer is not particularly limited, and various well-known methods can be used according to the material.

For example, in a case where a metal is used as the material for forming the colored layer, for example, a vapor phase deposition method (vacuum deposition method) such as vacuum deposition or sputtering, a film forming method using plating, or a method of bonding a foil formed of the above-described material can be used. From the viewpoint that a thin colored layer can be formed, a vacuum deposition is more preferable.

In addition, in a case where a pigment is used as the material for forming the colored layer, for example, a coating method or a printing method can be used.

In addition, a method of transferring a colored layer that is formed in advance can also be used.

In addition, the embodiment is not limited to the configuration where the colored layers are provided on the upper electrode 16 side and the lower electrode 14 side, respectively. The colored layer may be provided on at least one of the upper electrode 16 side or the lower electrode 14 side.

As described above, in the converter film 10, the piezoelectric layer 12 in which the piezoelectric particles 26 are dispersed in the viscoelastic matrix 24 that is formed of a polymer material having viscoelasticity at normal temperature is interposed between the upper electrode 16 and the lower electrode 14, and this laminate is interposed between the upper protective layer 20 and the lower protective layer 18.

In the converter film 10 having the above-described configuration, a maximum value at which a loss tangent (tan δ) at a frequency of 1 Hz in dynamic viscoelasticity measurement is 0.1 or higher is present at normal temperature.

As a result, even in a case where the converter film 10 undergoes significant bending deformation at a relatively low frequency of several Hz or lower due to external conditions, strain energy can be effectively diffused to the outside as heat. Therefore, the occurrence of cracking at an interface between the polymer matrix and the piezoelectric particles can be prevented.

A storage elastic modulus (E') of the converter film 10 at a frequency of 1 Hz in dynamic viscoelasticity measurement is 10 to 30 GPa at 0° C. and is 1 to 10 GPa at 50° C.

As a result, the converter film 10 can have a large frequency dispersion in storage elastic modulus (E') at normal temperature. That is, the converter film 10 is hard with respect to vibration at 20 Hz to 10 kHz and is flexible with respect to vibration of several Hz or lower.

In addition, in the converter film 10, the product of the thickness and the storage elastic modulus (E') at a frequency of 1 Hz in dynamic viscoelasticity measurement is preferably $1.0\times10^6$ to $2.0\times10^6$ (1.0E+06 to 2.0E+06) N/m at 0° C. and is preferably $1.0\times10^5$ to $1.0\times10^6$ (1.0E+05 to 1.0E+06) N/m at 50° C.

As a result, the converter film 10 can obtain appropriate rigidity and mechanical strength in a range where flexibility and acoustic characteristics do not deteriorate.

Further, in a master curve of the converter film 10 that is obtained from dynamic viscoelasticity measurement, a loss tangent (Tan δ) at a frequency of 1 kHz at 25° C. is preferably 0.05 or higher.

As a result, frequency characteristics of the pickup sensor including the converter film 10 are smooth, and when a minimum resonance frequency $f_0$ varies depending on a variation in the curvature of the converter film 10, a variation of sound quality can also be reduced.

Next, an example of a method of manufacturing the converter film 10 will be described with reference to FIGS. 13A to 13E.

Figure 13A:
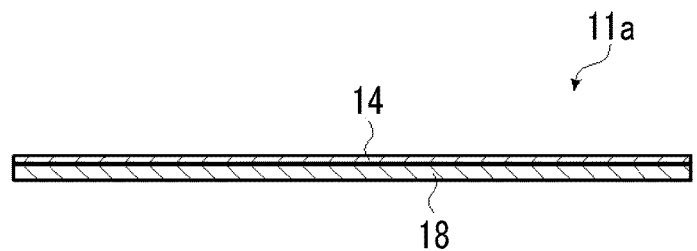
FIG. 13A is a schematic diagram showing an example of a method of preparing the electroacoustic converter film.

First, as shown in FIG. 13A, a sheet-like material 11a in which the lower electrode 14 is formed on the lower protective layer 18 is prepared. This sheet-like material 11a may be prepared by forming a copper thin film or the like as the lower electrode 14 on the surface of the lower protective layer 18 by vacuum deposition, sputtering, plating, or the like.

In a case where the lower protective layer 18 is extremely thin and handleability is poor, optionally, the lower protective layer 18 equipped with a separator (temporary support) may be used. As the separator, for example, a PET film having a thickness of 25 to 100 µm can be used. The separator may be removed immediately before forming a side surface insulating layer or the second protective layer and after thermal pressure bonding of the thin film electrode and the protective layer.

Alternatively, a commercially available product in which a copper thin film or the like is formed on the lower protective layer 18 may be used as the sheet-like material 11a.

On the other hand, a polymer material (hereinafter, also referred to as "viscoelastic material") having a cyanoethyl group such as cyanoethylated PVA is dissolved in an organic solvent, the piezoelectric particles 26 such as PZT particles are further added thereto, stirred, and dispersed. As a result, a paint is prepared. The organic solvent is not particularly limited, and various organic solvents such as dimethylformamide (DMF), methyl ethyl ketone, or cyclohexanone can be used.

Figure 13B:
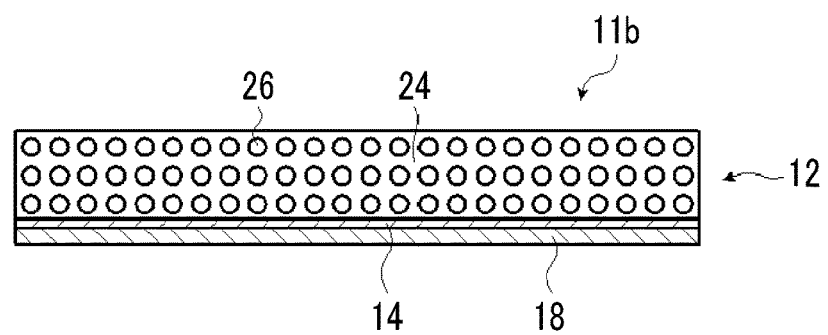
FIG. 13B is a schematic diagram showing the example of the method of preparing the electroacoustic converter film.

After the preparation of the sheet-like material 11a and the paint, the paint is cast (coated) on the sheet-like material, and the organic solvent is evaporated and dried. As a result, as shown in FIG. 13B, a laminate 11b in which the lower electrode 14 is formed on the lower protective layer 18 and the piezoelectric layer 12 is formed on the lower electrode 14 is prepared.

A casting method of the paint is not particularly limited, and all of the well-known methods (coating devices) such as a slide coater or a doctor coater can be used.

Alternatively, in a case where the viscoelastic material is a material such as cyanoethylated PVA that can be heated and melted, the viscoelastic material is heated and melted, and the polymer material and the piezoelectric particles 26 are added and dispersed to prepare a melt. Next, by extrusion molding or the like, this melt is extruded into a sheet shape on the sheet-like material 11a shown in FIG. 13A and cooled. As a result, the laminate 11b shown in FIG. 13B in which the lower electrode 14 is formed on the lower protective layer 18 and the piezoelectric layer 12 is formed on the lower electrode 14 may be prepared.

As described above, in the converter film 10, in addition to the viscoelastic material such as cyanoethylated PVA, a polymer piezoelectric material such as PVDF may also be added to the viscoelastic matrix 24.

In a case where the polymer piezoelectric material is added to the viscoelastic matrix 24, the polymer piezoelectric material to be added to the paint may be dissolved. Alternatively, the polymer piezoelectric material may be added to the molten viscoelastic material and then may be heated and melted.

After the preparation of the laminate 11b in which the lower electrode 14 is formed on the lower protective layer 18 and the piezoelectric layer 12 is formed on the lower electrode 14, polling of the piezoelectric layer 12 is performed.

A method of the polling of the piezoelectric layer 12 is not particularly limited, and a well-known method can be used. Preferable examples of the polling include a method shown in FIGS. 13C and 13D.

Figure 13C:
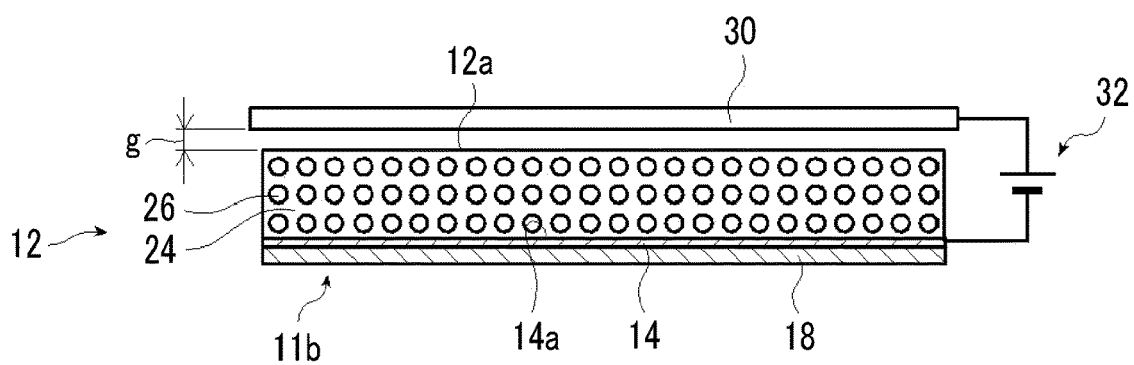
FIG. 13C is a schematic diagram showing the example of the method of preparing the electroacoustic converter film.
Figure 13D:
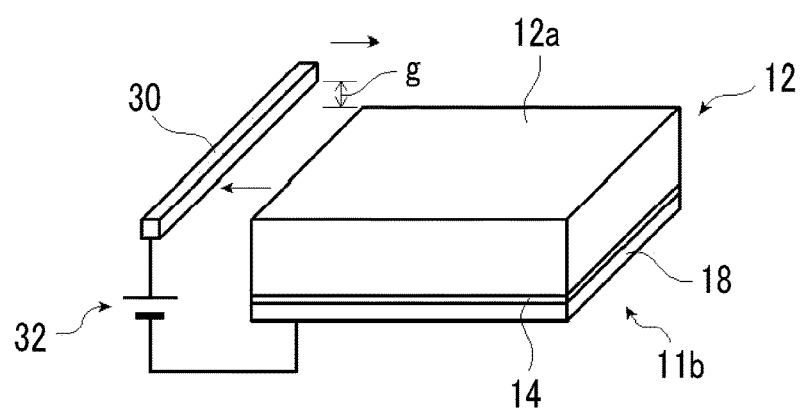
FIG. 13D is a schematic diagram showing the example of the method of preparing the electroacoustic converter film.

In this method, as shown in FIGS. 13C and 13D, a corona electrode 30 having a rod shape or a wire shape that is movable along an upper surface 12a of the piezoelectric layer 12 of the laminate 11b is provided above the upper surface 12a with a gap g of, for example, 1 mm. The corona electrode 30 and the lower electrode 14 are connected to a DC power supply 32.

Further, heating means for heating and holding the laminate 11b, for example, a hot plate is prepared.

For example, in a state the piezoelectric layer 12 is heated and held at a temperature of 100° C. using the heating means, corona discharge is generated by applying a DC voltage of several kV for example, 6 kV from the DC power supply 32 between the lower electrode 14 and the corona electrode 30. Further, in a state where the gap g is maintained, the corona electrode 30 moves (scans) along the upper surface 12a of the piezoelectric layer 12 to perform the polling of the piezoelectric layer 12.

In the polling using corona discharge (hereinafter, also referred to as "corona polling" for convenience of description), the corona electrode 30 may be moved using moving means of a well-known rod-shaped material.

In addition, in the corona polling, a method of moving the corona electrode 30 is not particularly limited. That is, the polling may be provided by fixing the corona electrode 30, providing a moving mechanism that moves the laminate 11b, and moving the laminate 11b. The laminate 11b may also be moved using moving means of a well-known sheet-like material.

Further, the number of corona electrodes 30 is not limited to one. The corona polling may be performed using a plurality of corona electrodes 30.

In addition, the polling is not limited to the corona polling, and typical electric field poling of directly applying a DC electric field to a target of the polling can also be used. However, in a case where the typical electric field poling is performed, it is necessary to form the upper electrode 16 before the polling.

In addition, before the polling, calendering of smoothing a surface of the piezoelectric layer 12 using a heating roller or the like may be performed. By performing the calendering, a thermal pressure bonding step described below can be smoothly performed.

While performing the polling of the piezoelectric layer 12 of the laminate 11b as described above, a sheet-like material 11c in which the upper electrode 16 is formed on the upper protective layer 20 is prepared. This sheet-like material 11c may be prepared by forming a copper thin film or the like as the upper electrode 16 on the surface of the upper protective layer 20 by vacuum deposition, sputtering, plating, or the like.

Figure 13E:
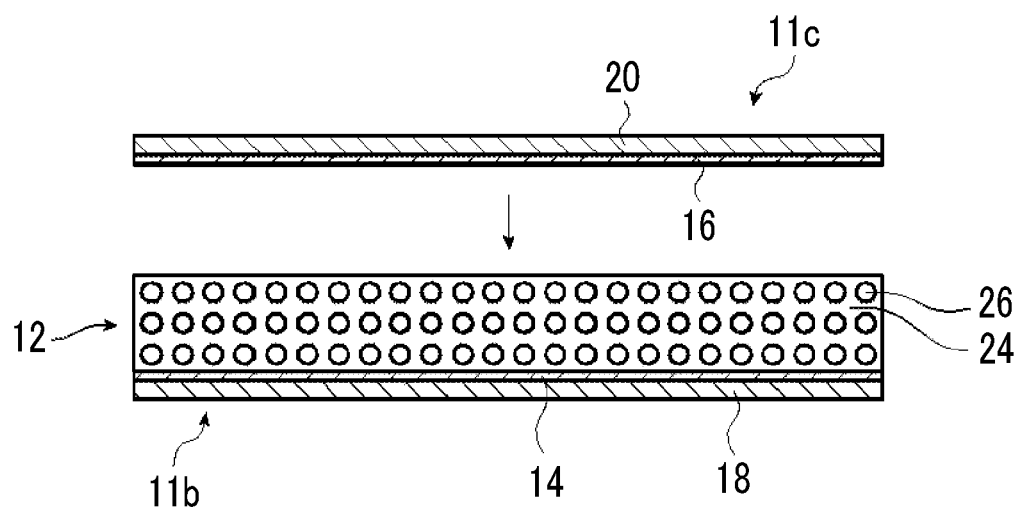
FIG. 13E is a schematic diagram showing the example of the method of preparing the electroacoustic converter film.

Next, as shown in FIG. 13E, the sheet-like material 11c is laminated on the laminate 11b having undergone the polling of the piezoelectric layer 12 such that the upper electrode 16 faces the piezoelectric layer 12.

Further, the laminate of the laminate 11b and the sheet-like material 11c is interposed between the upper protective layer 20 and the lower protective layer 18, and is thermally bonded using a hot press device, a pair of heating rollers, or the like. As a result, the converter film 10 is prepared.

The converter film 10 may be manufactured using the sheet-like material in the form of a cut sheet, or may be performed by roll-to-roll (hereinafter, also referred to as "R-to-R").

As is well known, R-to-R is a manufacturing method including: unwinding a raw material from a roll around which the elongated raw material is wound; performing various treatments such as film forming or surface treatment while transporting the raw material in a longitudinal direction; and winding the treated raw material again in a roll shape.

Hereinabove, the pickup sensor and the biological sensor according to the embodiment of the present invention have been described above. However, the present invention is not limited to the above-described examples, and various improvements and modifications can be made within a range not departing from the scope of the present invention.

EXAMPLES

Hereinafter, the present invention will be described in more detail using specific examples according to the present invention.

Example 1

The converter film 10 shown in FIG. 2 was prepared using the method shown in FIGS. 13A to 13E.

First, cyanoethylated PVA (CR-V, manufactured by Shin-Etsu Chemical Co., Ltd.) was dissolved in methyl ethyl ketone (MEK) at the following compositional ratio. Next, PZT particles were added to the solution at the following compositional ratio, and were dispersed using a propeller mixer (rotation speed: 2000 rpm). As a result, a paint for forming the piezoelectric layer 12 was prepared.

PZT particles: 1000 parts by mass
Cyanoethylated PVA: 100 parts by mass
MEK: 600 parts by mass In order to prepare the PZT particles, commercially available PZT raw material powder was sintered at 1000° C. to 1200° C., and was crushed and classified such that the average particle size was 3.5 μm.

On the other hand, each of the sheet-like materials 11a and 11c was prepared by forming a copper thin film having a thickness of 0.1 μm on a PET film having a thickness of 4 μm by vacuum deposition. That is, in the example, each of the upper electrode 16 and the lower electrode 14 is a copper-deposited thin film having a thickness of 0.1 μm, and each of the upper protective layer 20 and the lower protective layer 18 is a PET film having a thickness of 4 μm.

In order to obtain excellent handleability during the process, thermal pressure bonding of the thin film electrode and the protective layer was performed by using a PET film with a separator (temporary support PET) having a thickness of 50 μm as the PET film, and then the separator of each of the protective layers was removed.

The paint prepared as described above for forming the piezoelectric layer 12 was applied to the lower electrode 14 (copper-deposited thin film) of the sheet-like material 11a using a slide coater. The paint was applied such that the thickness of the dried coating film was 20 μm.

Next, the sheet-like material 11a to which the paint was applied was heated and dried in an oven at 120° C. to evaporate MEK. As a result, the laminate 11b in which the lower electrode 14 formed of copper was formed on the lower protective layer 18 formed of PET and the piezoelectric layer 12 having a thickness of 20 μm was formed on the lower electrode 14 was prepared.

Polling was performed on the piezoelectric layer 12 of the laminate 11b by the above-described corona polling shown in FIGS. 13C and 13D. The polling was performed by setting the temperature of the piezoelectric layer 12 to 100° C. and applying a DC voltage of 6 kV between the lower electrode 14 and the corona electrode 30 to generate corona discharge.

The sheet-like material 11c was laminated on the laminate 11b having undergone the polling.

Next, the laminate of the laminate 11b and the sheet-like material 11c is thermally bonded at 120° C. using a laminator. As a result, the piezoelectric layer 12, the upper electrode 16, and the lower electrode 14 adhered to each other, and thus the flat converter film 10 was prepared.

The prepared converter film 10 was cut into a size of 40 mm×40 mm, and the thin film electrode laminated on the main surface opposite to the abutting surface Sc was grounded. As a result, the pickup sensor 100a was prepared.

Comparative Example 1

Figure 14:
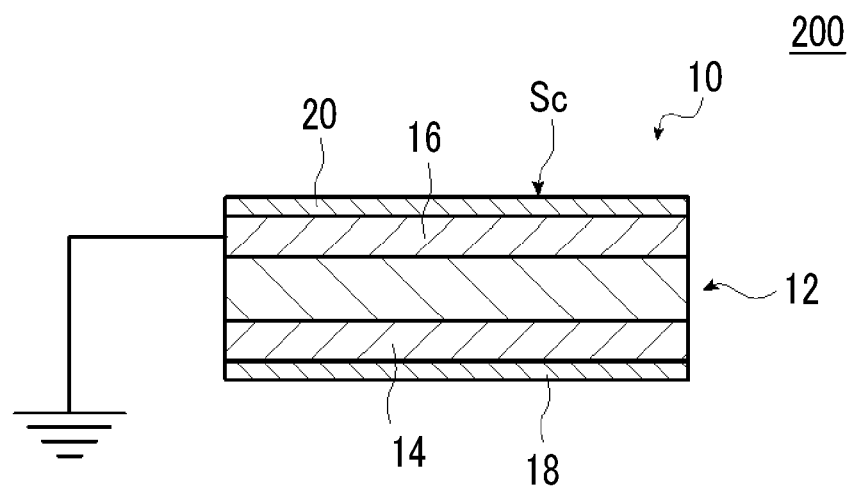
FIG. 14 is a cross-sectional view schematically showing a pickup sensor according to Comparative Example.

A pickup sensor 200 was prepared under the same conditions as in Example 1, except that the thin film electrode on the abutting surface Sc side was grounded as in the case of the pickup sensor 200 shown in FIG. 14.

Each of the pickup sensors according to Example 1 and Comparative Example 1 was bonded to the chest of a human body using a tape, and the heart rate was measured using vibration spectrum analysis software Spectra Plus (manufactured by Pioneer Hill Software LLC.).

Figure 15:
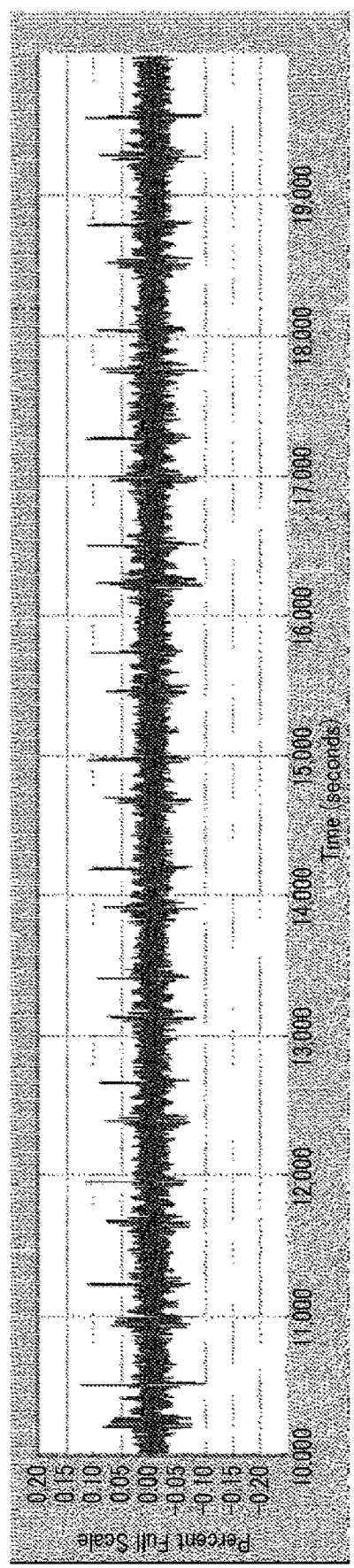
FIG. 15 is a graph showing a relationship between the intensity of a detected signal and the time.
Figure 16:
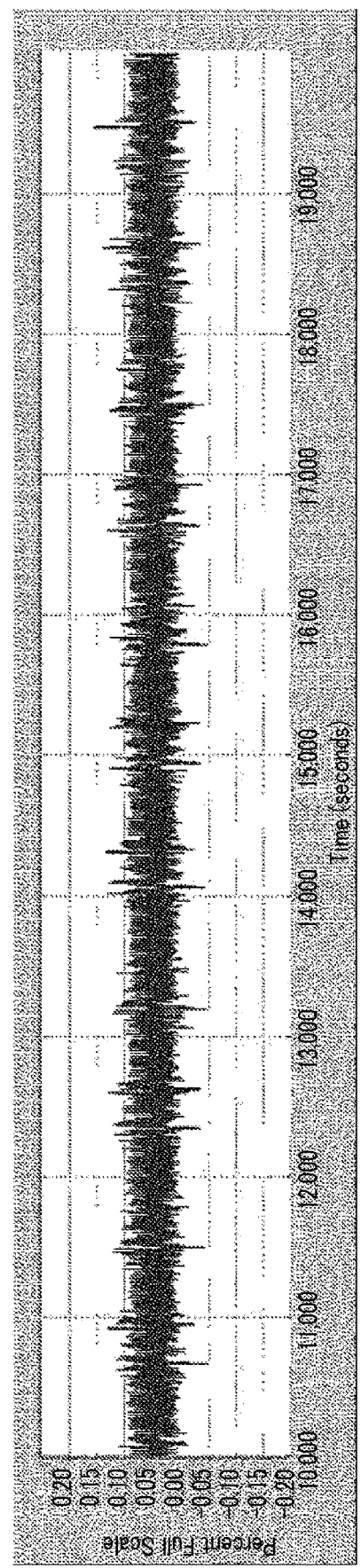
FIG. 16 is a graph showing a relationship between the intensity of a detected signal and the time.

FIG. 15 shows the measurement result of Example 1, and FIG. 16 shows the measurement result of Comparative Example 1. FIGS. 15 and 16 are graphs showing a relationship between the intensity of a detected signal and the time.

It can be seen from a comparison between FIGS. 15 and 16 that, in Example 1, the noise component is less than that in Comparative Example 1 and the heart rate can be detected efficiently and stably with high accuracy.

Example 2

The converter film 10 prepared as described in Example 1 was incorporated into the case 42 to prepare the converter unit 40.

Here, the size of the vibration region in the converter unit 40 was 40 mm×40 mm.

As the case 42, a rectangular box-shaped aluminum container with one open surface was used, in which the external size was 50 mm×50 mm, the size of the open surface was 40 mm×40 mm, the depth was 3 mm, and the thickness of the bottom plate was 1 mm.

In addition, the viscoelastic support 46 was disposed in the case 42. As the viscoelastic support 46, glass wool having a height of 25 mm and a density of 32 kg/m³ before assembly was used.

In addition, as the pressing member 48, a plate-shaped aluminum member was used, in which the size of the opening was 40 mm×40 mm.

The converter film 10 was disposed to cover the viscoelastic support 46 and the opening of the case 42, the peripheral portion thereof was fixed using the pressing member 48, and appropriate tension and curvature were applied to the converter film 10 using the viscoelastic support 46.

In addition, in the converter film 10, the thin film electrode on the main surface side in contact with the viscoelastic support 46 was grounded. As a result, the pickup sensor 100c shown in FIG. 5 was prepared.

The pickup sensors according to Example 2 was bonded to the chest of a human body using a tape, and the heart rate was measured under the same conditions as in Example 1.

Figure 17:
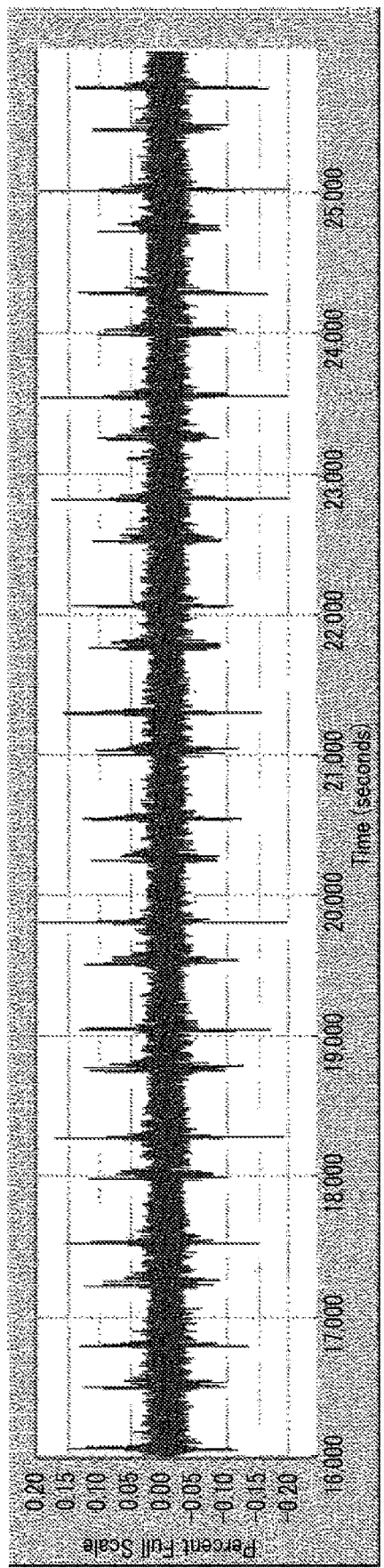
FIG. 17 is a graph showing a relationship between the intensity of a detected signal and the time.

FIG. 17 shows the measurement result of Example 2. FIG. 17 is a graph showing a relationship between the intensity of a detected signal and the time.

It can be seen from a comparison between FIGS. 17 and 15 that, in Example 2, the signal intensity of the noise component is equal to that in Example 1 but the signal intensity of the heart rate is higher.

Accordingly, it can be seen that micro vibration can be detected with high sensitivity by making the converter film 10 to be curved in a convex shape using the viscoelastic support 46.

Example 3

The converter unit 40 was prepared under the same conditions as in Example 2, except that the size of the vibration region was 10 mm×10 mm and the external size of the case 42 was 20 mm×20 mm.

The converter unit 40 was accommodated in the second case 50 in which the external size was φ30 mm, the size of the opening was 20 mm×20 mm, and the depth was 4 mm, and the suction cup member 52 was attached to the edge portion of the opening of the second case 50. As the suction cup member 52, a ring-shaped propylene rubber having an external size of φ40 mm was used.

Further, the holding member 54 was attached to the surface of the second case 50 opposite to the opening. As a result, the pickup sensor 100f shown in FIG. 12 was prepared.

Regarding the holding member 54, the material was aluminum, the wire diameter was 1 mm, and the curvature radius was about 80 mm.

The pickup sensors according to Example 3 was attached to the chest of a human body, and the heart rate was measured under the same conditions as in Example 1.

Figure 18:
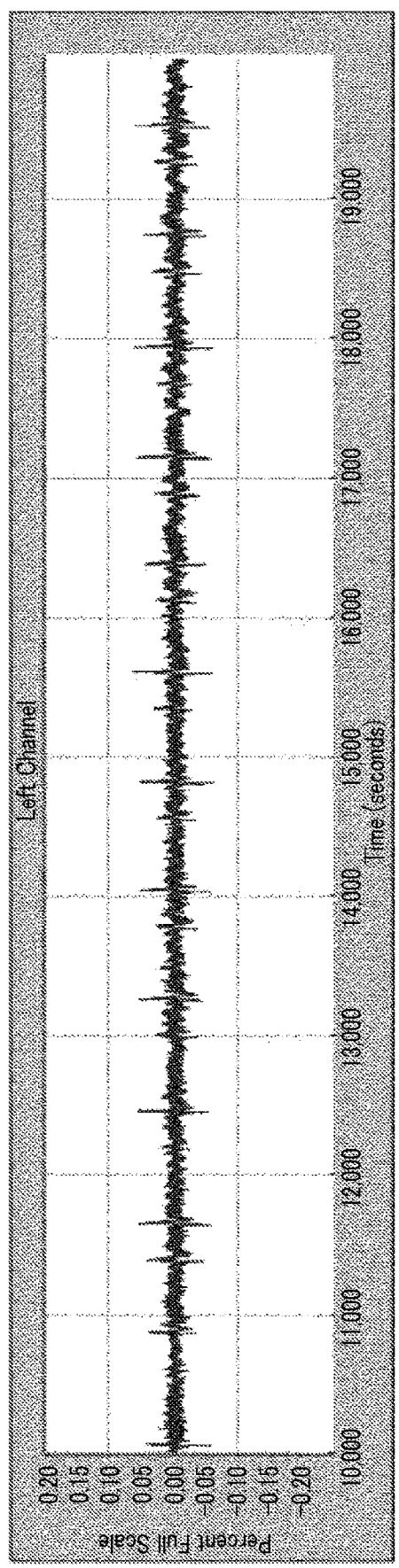
FIG. 18 is a graph showing a relationship between the intensity of a detected signal and the time.

FIG. 18 shows the measurement result of Example 3. FIG. 18 is a graph showing a relationship between the intensity of a detected signal and the time.

Example 4

A pickup sensor was prepared under the same conditions as in Example 3, except that the suction cup member 52 and the holding member 54 were not provided. This pickup sensor was bonded to the chest of a human body using a tape, and the heart rate was measured under the same conditions as in Example 1.

Figure 19:
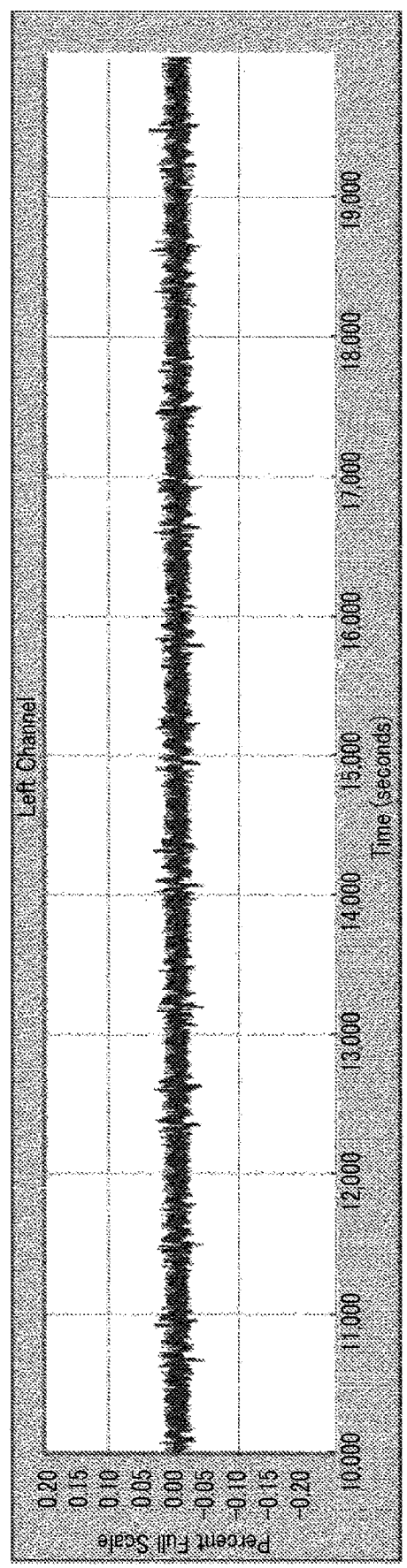
FIG. 19 is a graph showing a relationship between the intensity of a detected signal and the time.

FIG. 19 shows the measurement result of Example 4. FIG. 19 is a graph showing a relationship between the intensity of a detected signal and the time.

It can be seen from FIGS. 18 and 19 that, even in a case where the vibration detection portion (converter film) of the pickup sensor is small-sized, the signal intensity of the heart rate can be detected as a signal having a higher signal intensity than that of the noise component.

In addition, it can be seen from a comparison between FIGS. 18 and 19 that the configuration in which the pickup sensor is attached to a human body using the suction cup member 52 and the holding member 54 is preferable to the configuration in which the pickup sensor is attached to a test object using a tape because the signal of the heart rate can be detected as a high signal and the SN ratio can be further increased.

As can be seen from the above results, the effects of the present invention are obvious.

EXPLANATION OF REFERENCES

- 10: electroacoustic converter film
- 11a, 11c: sheet-like material
- 11b: laminate
- 12: piezoelectric layer
- 14: lower thin film electrode
- 16: upper thin film electrode
- 18: lower protective layer
- 20: upper protective layer
- 24: viscoelastic matrix
- 26: piezoelectric particle
- 30: corona electrode
- 32: DC power supply
- 40: electroacoustic converter unit
- 42: case
- 46: viscoelastic support
- 48: pressing member
- 50: second case
- 52: suction cup member
- 54: holding member
- 100a to 100f: pickup sensor
- Sc: abutting surface
- T: test object

What is claimed is:

1. A pickup sensor comprising an electroacoustic converter film including:
   a piezoelectric polymer composite in which piezoelectric particles are dispersed in a viscoelastic matrix that is formed of a polymer material having viscoelasticity at normal temperature;
   two thin film electrodes that are laminated on opposite surfaces of the piezoelectric polymer composite, respectively; and
   a protective layer that is laminated on at least one of the two thin film electrodes,
   wherein at least a part of a surface of the electroacoustic converter film is an abutting surface that abuts against a test object, and
   the thin film electrode on a surface of the electroacoustic converter film opposite to the abutting surface is grounded,
   wherein the electroacoustic converter film is folded, and
   the thin film electrode that is laminated on an outside main surface of the folded electroacoustic converter film is grounded, and
   wherein the protective layer is laminated on an outside main surface of the folded electroacoustic converter film.

2. The pickup sensor according to claim 1, wherein the electroacoustic converter film is curved and held so as to protrude to one main surface.

3. The pickup sensor according to claim 2, further comprising:
   an elastic support that is disposed to adhere to one main surface of the electroacoustic converter film such that the electroacoustic converter film is curved,
   wherein the elastic support is disposed to adhere to a main surface of the electroacoustic converter film on the grounded thin film electrode side.

4. The pickup sensor according to claim 3, further comprising:
   an elastic holding member that is formed in a C-shape,
   wherein the holding member presses and holds the electroacoustic converter film against the test object.

5. The pickup sensor according to claim 4, further comprising:
   a suction cup member,
   wherein the electroacoustic converter film is disposed at a center of an adsorption surface of the suction cup member.

6. A biological sensor comprising:
   the pickup sensor according to claim 5.

7. A biological sensor comprising:
   the pickup sensor according to claim 4.

8. A biological sensor comprising:
   the pickup sensor according to claim 3.

9. A biological sensor comprising:
   the pickup sensor according to claim 2.

10. A biological sensor comprising:
    the pickup sensor according to claim 1.

11. A pickup sensor comprising an electroacoustic converter film including:
    a piezoelectric polymer composite in which piezoelectric particles are dispersed in a viscoelastic matrix that is formed of a polymer material having viscoelasticity at normal temperature;
    two thin film electrodes that are laminated on opposite surfaces of the piezoelectric polymer composite, respectively; and
    a protective layer that is laminated on at least one of the two thin film electrodes, wherein at least a part of a surface of the electroacoustic converter film is an abutting surface that abuts against a test object, and the thin film electrode on a surface of the electroacoustic converter film opposite to the abutting surface is grounded, wherein the pickup sensor further comprises:

an elastic support that is disposed to adhere to one main surface of the electroacoustic converter film such that the electroacoustic converter film is curved, and wherein the elastic support is disposed to adhere to a main surface of the electroacoustic converter film on the grounded thin film electrode side.

12. A biological sensor comprising:
the pickup sensor according to claim 11.

13. A pickup sensor comprising an electroacoustic converter film including:

a piezoelectric polymer composite in which piezoelectric particles are dispersed in a viscoelastic matrix that is formed of a polymer material having viscoelasticity at normal temperature;

two thin film electrodes that are laminated on opposite surfaces of the piezoelectric polymer composite, respectively; and a protective layer that is laminated on at least one of the two thin film electrodes, wherein at least a part of a surface of the electroacoustic converter film is an abutting surface that abuts against a test object, and the thin film electrode on a surface of the electroacoustic converter film opposite to the abutting surface is grounded, wherein the pickup sensor further comprises:

an elastic holding member that is formed in a C-shape, and wherein the holding member presses and holds the electroacoustic converter film against the test object.

14. A biological sensor comprising:
the pickup sensor according to claim 13.

15. A pickup sensor comprising an electroacoustic converter film including:

a piezoelectric polymer composite in which piezoelectric particles are dispersed in a viscoelastic matrix that is formed of a polymer material having viscoelasticity at normal temperature;

two thin film electrodes that are laminated on opposite surfaces of the piezoelectric polymer composite, respectively; and a protective layer that is laminated on at least one of the two thin film electrodes, wherein at least a part of a surface of the electroacoustic converter film is an abutting surface that abuts against a test object, and the thin film electrode on a surface of the electroacoustic converter film opposite to the abutting surface is grounded, wherein the pickup sensor further comprises:

a suction cup member, and wherein the electroacoustic converter film is disposed at a center of an adsorption surface of the suction cup member.

16. A biological sensor comprising:
the pickup sensor according to claim 15.

* * * * *